(12) United States Patent
Modesitt

(10) Patent No.: US 7,390,328 B2
(45) Date of Patent: Jun. 24, 2008

(54) DEVICE AND METHOD FOR SUTURING OF INTERNAL PUNCTURE SITES

(75) Inventor: D. Bruce Modesitt, San Carlos, CA (US)

(73) Assignee: Abbott Laboratories, Abbott Park, IL (US)

( * ) Notice: Subject to any disclaimer, the term of this patent is extended or adjusted under 35 U.S.C. 154(b) by 786 days.

(21) Appl. No.: 10/742,406

(22) Filed: Dec. 19, 2003

(65) Prior Publication Data
US 2005/0149065 A1    Jul. 7, 2005

(51) Int. Cl.
*A61B 17/04* (2006.01)
(52) U.S. Cl. ......................... 606/144; 128/898
(58) Field of Classification Search ................ 606/139, 606/144, 145, 147, 148, 151, 213, 222, 224; 128/898
See application file for complete search history.

(56) References Cited

U.S. PATENT DOCUMENTS

| | | | |
|---|---|---|---|
| 312,408 | A | 2/1885 | Wackerhagen |
| 597,165 | A | 1/1898 | Hall |
| 659,422 | A | 10/1900 | Shidler |
| 989,231 | A | 4/1911 | Davis |
| 2,127,903 | A | 8/1938 | Bowen |
| 2,397,823 | A | 4/1946 | Walter |
| 2,588,589 | A | 3/1952 | Tauber |
| 2,646,045 | A | 7/1953 | Priestley |
| 2,692,599 | A | 10/1954 | Creelman |
| 2,959,172 | A | 11/1960 | Held |
| 3,033,156 | A | 5/1962 | Verlish |

(Continued)

FOREIGN PATENT DOCUMENTS

DE    42 10 724    7/1993

(Continued)

OTHER PUBLICATIONS

"Innovation Through Progress," REMA-Medizintechnik GmbH, Durbheim-Tuttlingen, Germany.

(Continued)

*Primary Examiner*—Michael J. Hayes
*Assistant Examiner*—Victor Nguyen
(74) *Attorney, Agent, or Firm*—Workman Nydegger

(57) ABSTRACT

A method of closing a puncture in a blood vessel wall, including: positioning a suture placement device in a tissue tract and into a puncture in the blood vessel wall, the placement device having a length of suture with a first end, a second end and a bight between the first and second ends with the bight being prearranged on the device to define a pre-tied knot when the first end of the suture passes through the bight; advancing the first end of the length of suture in a distal direction from the device through a first penetration in the blood vessel wall adjacent to the puncture; guiding the suture length from the first penetration across a proximal side of the puncture to a second penetration adjacent to the puncture opposite the first penetration; and advancing the suture length in a proximal direction through the second penetration, through the device, and through the bight so that the two ends of the suture length are accessible external to the tissue tract for securing the suture across the puncture to close the puncture.

12 Claims, 20 Drawing Sheets

U.S. PATENT DOCUMENTS

| | | | |
|---|---|---|---|
| 3,104,666 A | 9/1963 | Hale et al. | |
| 3,470,875 A | 10/1969 | Johnson | |
| 3,653,388 A | 4/1972 | Tenckhoff | |
| 3,665,926 A | 5/1972 | Flores | |
| 3,776,237 A | 12/1973 | Hill et al. | |
| 3,820,544 A | 6/1974 | Semm | |
| 3,918,455 A | 11/1975 | Coplan | |
| 3,926,194 A | 12/1975 | Greenberg et al. | |
| 3,939,820 A | 2/1976 | Grayzel | |
| 4,018,228 A | 4/1977 | Goosen | |
| 4,109,658 A | 8/1978 | Hughes | |
| 4,135,623 A | 1/1979 | Thyen | |
| 4,161,951 A | 7/1979 | Scanlan, Jr. | |
| 4,168,073 A | 9/1979 | LaRue | |
| 4,182,339 A | 1/1980 | Hardy, Jr. | |
| 4,185,636 A | 1/1980 | Gabbay et al. | |
| 4,216,776 A | 8/1980 | Downie et al. | |
| 4,217,665 A | 8/1980 | Bex et al. | |
| 4,235,177 A | 11/1980 | Arbuckle | |
| 4,317,445 A | 3/1982 | Robinson | |
| 4,411,654 A | 10/1983 | Boarini et al. | |
| 4,412,832 A | 11/1983 | Kling et al. | |
| 4,437,465 A | 3/1984 | Nomoto et al. | |
| 4,492,229 A | 1/1985 | Grunwald | |
| 4,493,323 A | 1/1985 | Albright et al. | |
| 4,553,543 A | 11/1985 | Amarasinghe | |
| 4,586,614 A | 5/1986 | Ger | |
| 4,587,969 A | 5/1986 | Gillis | |
| 4,596,559 A | 6/1986 | Fleischhacker | |
| 4,629,450 A | 12/1986 | Suzuki et al. | |
| 4,651,733 A | 3/1987 | Mobin-Uddin | |
| 4,702,250 A | 10/1987 | Ovil et al. | |
| 4,723,549 A | 2/1988 | Wholey et al. | |
| 4,738,666 A | 4/1988 | Fuqua | |
| 4,744,364 A | 5/1988 | Kensey | |
| 4,803,984 A | 2/1989 | Narayanan et al. | |
| 4,836,205 A | 6/1989 | Barrett | |
| 4,852,568 A * | 8/1989 | Kensey | 606/213 |
| 4,890,612 A | 1/1990 | Kensey | |
| 4,898,155 A | 2/1990 | Ovil et al. | |
| 4,911,164 A | 3/1990 | Roth | |
| 4,926,860 A | 5/1990 | Stice et al. | |
| 4,929,246 A | 5/1990 | Sinofsky | |
| 4,935,027 A | 6/1990 | Yoon | |
| 4,957,498 A | 9/1990 | Caspari et al. | |
| 4,983,168 A | 1/1991 | Moorehead | |
| 4,984,581 A | 1/1991 | Stice | |
| 5,002,563 A | 3/1991 | Pyka et al. | |
| 5,009,643 A | 4/1991 | Reich et al. | |
| 5,021,059 A | 6/1991 | Kensey et al. | |
| 5,037,433 A | 8/1991 | Wilk et al. | |
| 5,047,039 A | 9/1991 | Avant et al. | |
| 5,059,201 A | 10/1991 | Asnis | |
| 5,061,274 A | 10/1991 | Kensey | |
| 5,078,721 A | 1/1992 | McKeating | |
| 5,080,664 A | 1/1992 | Jain | |
| 5,100,419 A | 3/1992 | Ehlers | |
| 5,100,432 A | 3/1992 | Matsutani | |
| 5,109,780 A | 5/1992 | Slouf et al. | |
| 5,129,913 A | 7/1992 | Ruppert | |
| 5,147,373 A | 9/1992 | Ferzli | |
| 5,160,339 A | 11/1992 | Chen et al. | |
| 5,171,251 A | 12/1992 | Bregen et al. | |
| 5,192,294 A | 3/1993 | Blake, III | |
| 5,192,301 A | 3/1993 | Kamiya et al. | |
| 5,192,302 A | 3/1993 | Kensey et al. | |
| 5,207,703 A | 5/1993 | Jain | |
| 5,217,470 A | 6/1993 | Weston | |
| 5,219,358 A | 6/1993 | Bendel et al. | |
| 5,222,974 A | 6/1993 | Kensey et al. | |
| 5,234,443 A | 8/1993 | Phan et al. | |
| 5,242,427 A | 9/1993 | Bilweis | |
| 5,250,033 A | 10/1993 | Evans et al. | |
| 5,250,053 A | 10/1993 | Snyder | |
| 5,254,126 A | 10/1993 | Filipi et al. | |
| 5,258,003 A | 11/1993 | Ciaglia et al. | |
| 5,279,311 A | 1/1994 | Snyder | |
| 5,281,236 A | 1/1994 | Bagnato et al. | |
| 5,281,237 A | 1/1994 | Gimpelson | |
| 5,285,945 A | 2/1994 | Brinkerhoff et al. | |
| 5,289,963 A | 3/1994 | McGarry et al. | |
| 5,290,284 A | 3/1994 | Adair | |
| 5,290,297 A | 3/1994 | Phillips | |
| 5,292,309 A | 3/1994 | Van Tassel et al. | |
| 5,292,332 A | 3/1994 | Lee | |
| 5,293,881 A | 3/1994 | Green et al. | |
| 5,295,993 A | 3/1994 | Green | |
| 5,300,085 A | 4/1994 | Yock | |
| 5,304,184 A * | 4/1994 | Hathaway et al. | 606/144 |
| 5,304,185 A | 4/1994 | Taylor | |
| 5,306,254 A | 4/1994 | Nash et al. | |
| 5,312,024 A | 5/1994 | Grant et al. | |
| 5,320,632 A | 6/1994 | Heidmueller | |
| 5,336,229 A | 8/1994 | Noda | |
| 5,336,230 A | 8/1994 | Leichtling et al. | |
| 5,336,231 A | 8/1994 | Adair | |
| 5,342,369 A | 8/1994 | Harryman, II | |
| 5,353,974 A | 10/1994 | Brinkerhoff et al. | |
| 5,354,312 A | 10/1994 | Brinkerhoff et al. | |
| 5,364,408 A | 11/1994 | Gordon | |
| 5,368,595 A | 11/1994 | Lewis | |
| 5,368,601 A | 11/1994 | Sauer et al. | |
| 5,374,275 A | 12/1994 | Bradley et al. | |
| 5,376,096 A | 12/1994 | Foster | |
| 5,383,896 A | 1/1995 | Gershony et al. | |
| 5,385,569 A | 1/1995 | Swor | |
| 5,387,221 A | 2/1995 | Bisgaard | |
| 5,387,227 A | 2/1995 | Grice | |
| 5,395,332 A | 3/1995 | Ressemann et al. | |
| 5,395,349 A | 3/1995 | Quiachon et al. | |
| 5,397,310 A | 3/1995 | Chu et al. | |
| 5,397,325 A | 3/1995 | Della Badia et al. | |
| 5,403,329 A | 4/1995 | Hinchcliffe | |
| 5,403,338 A | 4/1995 | Milo | |
| 5,411,481 A | 5/1995 | Allen et al. | |
| 5,413,571 A | 5/1995 | Katsaros et al. | |
| 5,417,699 A | 5/1995 | Klein et al. | |
| 5,425,705 A | 6/1995 | Evard et al. | |
| 5,431,666 A | 7/1995 | Sauer et al. | |
| 5,433,700 A | 7/1995 | Peters | |
| 5,452,733 A | 9/1995 | Sterman et al. | |
| 5,454,822 A | 10/1995 | Schob et al. | |
| 5,454,834 A | 10/1995 | Boebel et al. | |
| 5,458,574 A | 10/1995 | Machold et al. | |
| 5,470,338 A | 11/1995 | Whitfield et al. | |
| 5,476,469 A | 12/1995 | Hathaway et al. | |
| 5,476,470 A | 12/1995 | Fitzgibbons, Jr. | |
| 5,478,309 A | 12/1995 | Sweezer et al. | |
| 5,478,353 A | 12/1995 | Yoon | |
| 5,480,407 A | 1/1996 | Wan et al. | |
| 5,486,190 A | 1/1996 | Green | |
| 5,489,295 A | 2/1996 | Piplani et al. | |
| 5,496,332 A | 3/1996 | Sierra et al. | |
| 5,507,744 A | 4/1996 | Tay et al. | |
| 5,507,755 A | 4/1996 | Gresl et al. | |
| 5,507,757 A | 4/1996 | Sauer et al. | |
| 5,507,758 A | 4/1996 | Thomason et al. | |
| 5,509,902 A | 4/1996 | Raulerson | |
| 5,520,655 A | 5/1996 | Davila et al. | |
| 5,520,665 A | 5/1996 | Fleetwood | |
| 5,520,702 A | 5/1996 | Sauer et al. | |
| 5,527,321 A | 6/1996 | Hinchliffe | |
| 5,527,322 A | 6/1996 | Klein et al. | |
| D372,310 S | 7/1996 | Hartnett | |

| | | |
|---|---|---|
| 5,531,700 A | 7/1996 | Moore et al. |
| 5,540,701 A | 7/1996 | Sharkey et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,554,162 A | 9/1996 | DeLange |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,573,540 A | 11/1996 | Yoon |
| 5,591,179 A | 1/1997 | Edelstein |
| 5,591,206 A | 1/1997 | Moufarrege |
| 5,593,421 A | 1/1997 | Bauer |
| 5,603,718 A | 2/1997 | Xu |
| 5,607,435 A | 3/1997 | Sachdeva et al. |
| 5,611,794 A | 3/1997 | Sauer et al. |
| 5,613,974 A | 3/1997 | Andreas et al. |
| 5,613,975 A | 3/1997 | Christy |
| 5,643,289 A | 7/1997 | Sauer et al. |
| 5,669,917 A | 9/1997 | Sauer et al. |
| 5,700,273 A | 12/1997 | Buelna et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,728,151 A | 3/1998 | Garrison et al. |
| 5,741,276 A | 4/1998 | Poloyko et al. |
| 5,741,280 A | 4/1998 | Fleenor |
| 5,759,188 A | 6/1998 | Yoon |
| 5,766,183 A | 6/1998 | Sauer |
| 5,766,186 A | 6/1998 | Faraz et al. |
| 5,779,719 A | 7/1998 | Klein et al. |
| 5,792,151 A | 8/1998 | Heck et al. |
| 5,792,152 A | 8/1998 | Klein et al. |
| 5,799,661 A | 9/1998 | Boyd et al. |
| 5,810,850 A | 9/1998 | Hathaway et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,990 A | 1/1999 | Nobles et al. |
| 5,860,991 A | 1/1999 | Klein et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,951,590 A | 9/1999 | Goldfarb |
| 5,954,732 A | 9/1999 | Hart et al. |
| 5,972,030 A | 10/1999 | Garrison et al. |
| 6,036,699 A | 3/2000 | Andreas et al. |
| 6,048,351 A | 4/2000 | Gordon et al. |
| 6,117,144 A | 9/2000 | Nobles et al. |
| 6,136,010 A | 10/2000 | Modesitt et al. |
| 6,190,396 B1 | 2/2001 | Whitin et al. |
| 6,206,893 B1 | 3/2001 | Klein et al. |
| 6,355,050 B1 | 3/2002 | Andreas et al. |
| 6,358,258 B1 | 3/2002 | Arcia et al. |
| 6,436,109 B1 | 8/2002 | Kontos |
| 6,517,553 B2 | 2/2003 | Klein et al. |
| 6,558,399 B1 | 5/2003 | Isbell et al. |
| 6,641,592 B1 | 11/2003 | Sauer et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,179,266 B2 | 2/2007 | Kontos |
| 2002/0095164 A1 | 7/2002 | Andreas |
| 2003/0093093 A1 | 5/2003 | Modesitt et al. |
| 2004/0097978 A1 | 5/2004 | Modesitt et al. |
| 2004/0186487 A1 | 9/2004 | Klein |
| 2005/0171561 A1 | 8/2005 | Songer |
| 2006/0167476 A1 | 7/2006 | Burdulis |
| 2006/0167477 A1 | 7/2006 | Arcia |
| 2006/0173469 A1 | 8/2006 | Klein |

FOREIGN PATENT DOCUMENTS

| | | |
|---|---|---|
| DE | 9217932 | 7/1993 |
| EP | 0 140 557 | 5/1985 |
| EP | 0140557 | 5/1985 |
| EP | 0 207 545 | 1/1987 |
| EP | 0 474 887 | 3/1992 |
| EP | 0 478 358 | 4/1992 |
| EP | 0478 887 | 4/1992 |
| EP | 0 589 409 | 9/1992 |
| EP | 0 624 343 | 4/1993 |
| EP | 0 542 126 | 5/1993 |
| EP | 0 568 098 | 11/1993 |
| EP | 0 669 101 | 8/1995 |
| EP | 0 669 102 | 8/1995 |
| EP | 0 669 103 | 8/1995 |
| EP | 0 684 012 A2 | 11/1995 |
| FR | 1059544 | 3/1954 |
| JP | 2119866 A | 5/1990 |
| JP | 405042161 | 2/1993 |
| SU | 280810 | 4/1981 |
| SU | 993922 | 2/1983 |
| SU | 1-03-329 A | 5/1984 |
| SU | 1093329 | 5/1984 |
| SU | 1174-036 A | 8/1985 |
| SU | 1174036 | 8/1985 |
| SU | 1544383 | 2/1990 |
| SU | 1648400 | 5/1991 |
| WO | WO 85/03858 | 9/1985 |
| WO | 9405213 | 3/1994 |
| WO | WO 94/27503 | 12/1994 |
| WO | WO 94/28801 | 12/1994 |
| WO | WO 9505121 | 2/1995 |
| WO | WO 95/13021 | 5/1995 |
| WO | WO 95/35065 | 12/1995 |
| WO | WO 97/03613 | 2/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 98/04195 | 2/1998 |
| WO | WO 98/42262 | 10/1998 |
| WO | WO 00/12013 | 3/2000 |
| WO | WO 00/51498 | 9/2000 |
| WO | WO 01/19259 | 3/2001 |
| WO | WO 02/36021 | 5/2002 |
| WO | WO 05/65549 | 7/2005 |

OTHER PUBLICATIONS

Elgiloy® Brochure, Jun. 23, 1959, Elgin National Watch Company, Elgin, Illinois.

Product Brochure "The Proven Solution to Endoscopic Suturing," Laurus Medical Corporation, Irvine, CA, Oct. 1994.

Catherine B. Faulkner, Letter regarding "VasoSeal Vascular Hemostasis," *Datascope*, New Jersey, 1 page only.

Product Brochure, "SuperStitch—Closure Made Simple™," Sutura, Inc.

U.S. Appl. No. 09/608,832, filed Jun. 30, 2000, Burdulis.

U.S. Appl. No. 09/610,564, filed Jun. 30, 2000, Burdulis.

Cardiac Catheterization and Angiography, 3rd Ed., Lea & Febiger, Philadelphia, 1986.

Cardio-Thoracic Systems Prospectus dated Mar. 20, 1996.
Elgin National Watch Company, Product Brochure entitled "Elgiloy, A Cobalt Nickel Spring Alloy", 33 pages.
Faulkner, Catherine B., Letter regarding "VasoSeal Vascular Hemostasis", *Datascope*, New Jersey, 1 page.
Kensey Nash Corporation, Exton, PA, "The Hemostatic Puncture Closure Device", 2 pages.
Laurus Nash Corporation, "Endoscopic Suturing Made Simple", The Laurus ND-2600 Needle Driver, Irvine, CA. 1 page.
The Laurus In-Line Endoscopic Suturing Device (Oct. 1994) 1 page.
Patent No. 5,417,699, Office Action, May 12, 1993.
Patent No. 5,417,699, Office Action, Aug. 1, 1994.
Patent No. 5,417,699, Notice of Allowance, Nov. 3, 1994.
Patent No. 5,417,699, Issue Notification, Apr. 17, 1995.
Patent No. 5,527,322, Office Action, Sep. 16, 1994.
Patent No. 5,527,322, Office Action, May 30, 1995.
Patent No. 5,527,322, Office Action, Oct. 26, 1995.
Patent No. 5,527,322, Notice of Allowance, Dec. 15, 1995.
Patent No. 5,527,322, Issue Notification, May 13, 1996.
Patent No. 5,613,974, Office Action, Jun. 5, 1995.
Patent No. 5,613,974, Office Action, Jan. 5, 1996.
Patent No. 5,613,974, Notice of Allowance, May 22, 1996.
Patent No. 5,613,974, Issue Notification, Feb. 18, 1997.
Patent No. 5,779,719, Office Action, Jun. 1, 1995.
Patent No. 5,779,719, Notice of Allowance, Feb. 6, 1998.
Patent No. 5,779,719, Issue Notification, Jun. 6, 1998.
Patent No. 5,792,152, Office Action, Jan. 21, 1997.
Patent No. 5,792,152, Notice of Allowance, Oct. 17, 1997.
Patent No. 5,792,152, Issue Notification, Jul. 7, 1998.
Patent No. 6,036,699, Office Action, Sep. 14, 1998.
Patent No. 6,036,699, Office Action, Apr. 13, 1999.
Patent No. 6,036,699, Notice of Allowance, Jul. 15, 1999.
Patent No. 6,036,699, Issue Notification, Mar. 2, 2000.
Patent No. 6,206,893, Office Action, Jul. 10, 2000.
Patent No. 6,206,893, Notice of Allowance, Oct. 25, 2000.
Patent No. 6,206,893, Issue Notification, Mar. 9, 2001.
Patent No. 6,355,050, Office Action, Jul. 23, 1998.
Patent No. 6,355,050, Office Action, Oct. 13, 1999.
Patent No. 6,355,050, Office Action, Oct. 23, 2000.
Patent No. 6,355,050, Office Action, Jul. 11, 2001.
Patent No. 6,355,050, Notice of Allowance, Sep. 11, 2001.
Patent No. 6,355,050, Issue Notification, Feb. 21, 2002.
Patent No. 6,358,258, Office Action, Nov. 6, 2000.
Patent No. 6,358,258, Notice of Allowance, Apr. 20, 2001.
Patent No. 6,358,258, Notice of Allowance, Sep. 10, 2001.
Patent No. 6,358,258, Issue Notification, Mar. 1, 2002.
Patent No. 6,517,553, Office Action, Oct. 23, 2001.
Patent No. 6,517,553, Office Action, Jun. 17, 2002.
Patent No. 6,517,553, Notice of Allowance, Sep. 9, 2002.
Patent No. 6,517,553, Issue Notification, Jan. 23, 2003.
Patent No. 6,558,399, Office Action, Jul. 11, 2001.
Patent No. 6,558,399, Notice of Allowance, Dec. 24, 2002.
Patent No. 6,558,399, Issue Notification, Apr. 17, 2003.
Patent No. 7,029,480, Office Action, Mar. 17, 2005.
Patent No. 7,029,480, Office Action, Jun. 10, 2005.
Patent No. 7,029,480, Notice of Allowance, Nov. 17, 2005.
Patent No. 7,029,480, Issue Notification, Mar. 29, 2005.
Patent No. 7,029,481, Office Action, Feb. 16, 2005.
Patent No. 7,029,481, Office Action, Jul. 7, 2005.
Patent No. 7,029,481, Notice of Allowance, Nov. 15, 2005.
Patent No. 7,029,481, Issue Notification, Mar. 29, 2006.
Patent No. 7,048,747, Office Action, Mar. 17, 2004.
Patent No. 7,048,747, Office Action, Feb. 28, 2005.
Patent No. 7,048,747, Office Action, May 25, 2005.
Patent No. 7,048,747, Office Action, Aug. 24, 2005.
Patent No. 7,048,747, Office Action, Nov. 8, 2005.
Patent No. 7,048,747, Notice of Allowance, Dec. 13, 2005.
Patent No. 7,048,747, Issue Notification, May 3, 2006.
Patent No. 2002/0095164, Office Action, Sep. 30, 2003.
Patent No. 2004/0186487, Office Action, Sep. 5, 2006.
Patent No. 2004/0186487, Office Action, Jul. 16, 2007.
Patent No. 2005/0171561, Office Action, Nov. 2, 2005.
Patent No. 2005/0171561, Office Action, Feb. 16, 2006.
Patent No. 2005/0171561, Office Action, Oct. 19, 2006.
Patent No. 2005/0171561, Office Action, Jun. 7, 2007.
Patent No. 2005/0167476, Notice of Allowance, Sep. 20, 2007.
Patent No. 2006/0167477, Office Action, Sep. 7, 2007.
US 5,820,544, 06/1974, Semm (withdrawn)

* cited by examiner

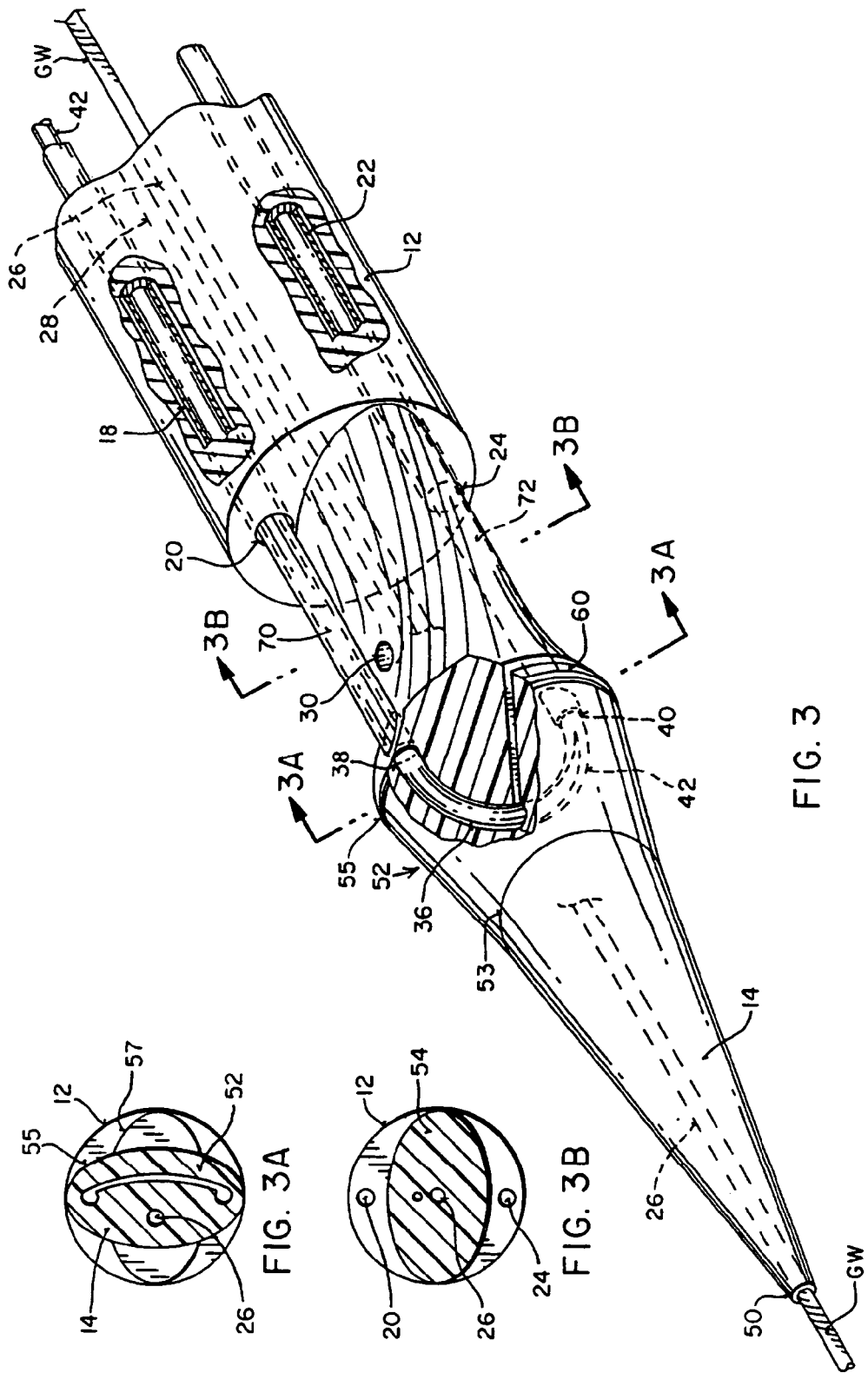

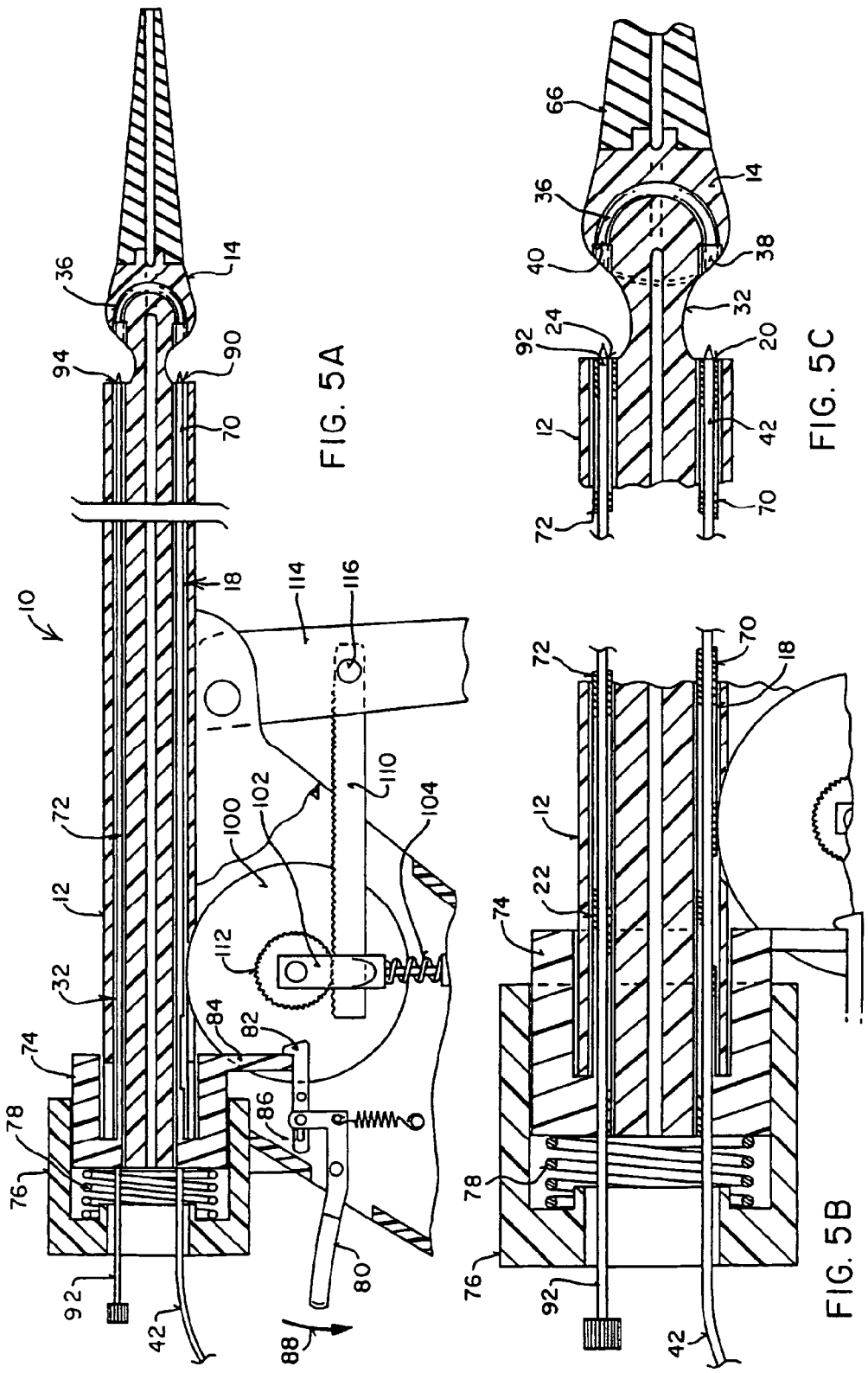

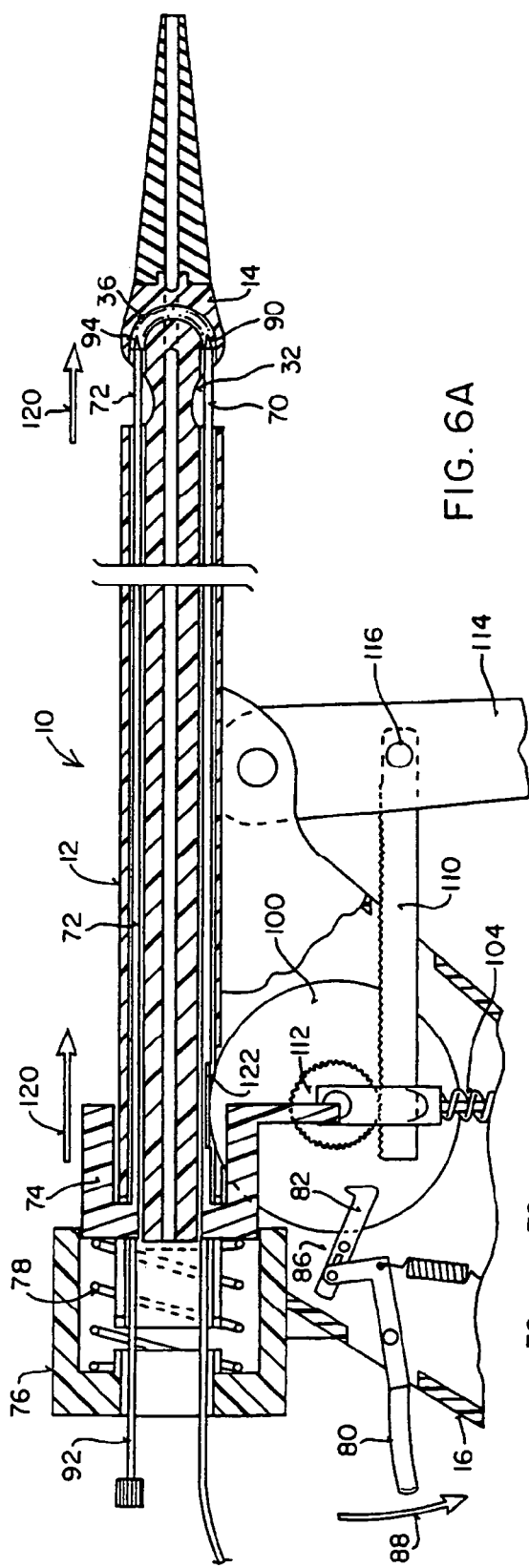
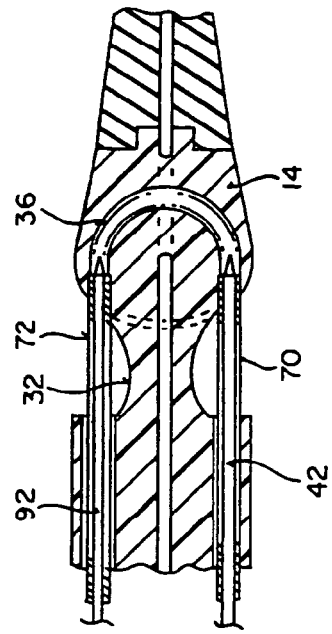
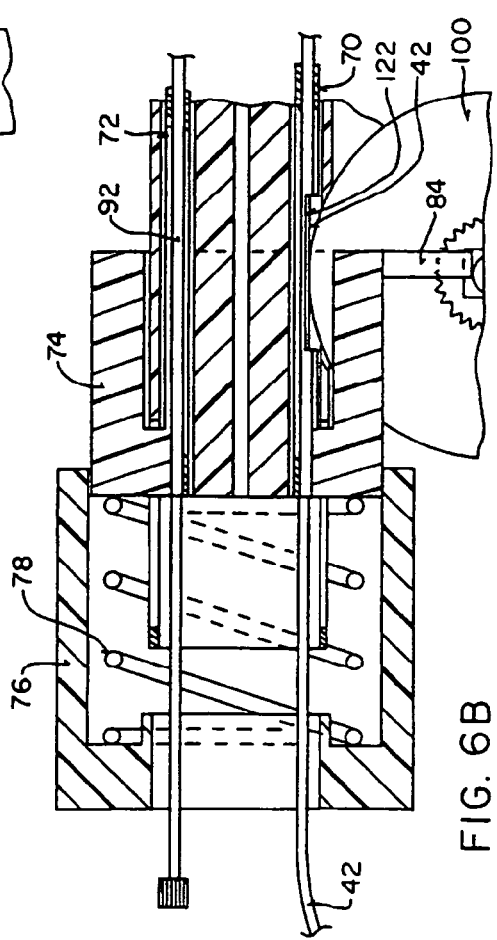
FIG. 6A
FIG. 6C
FIG. 6B

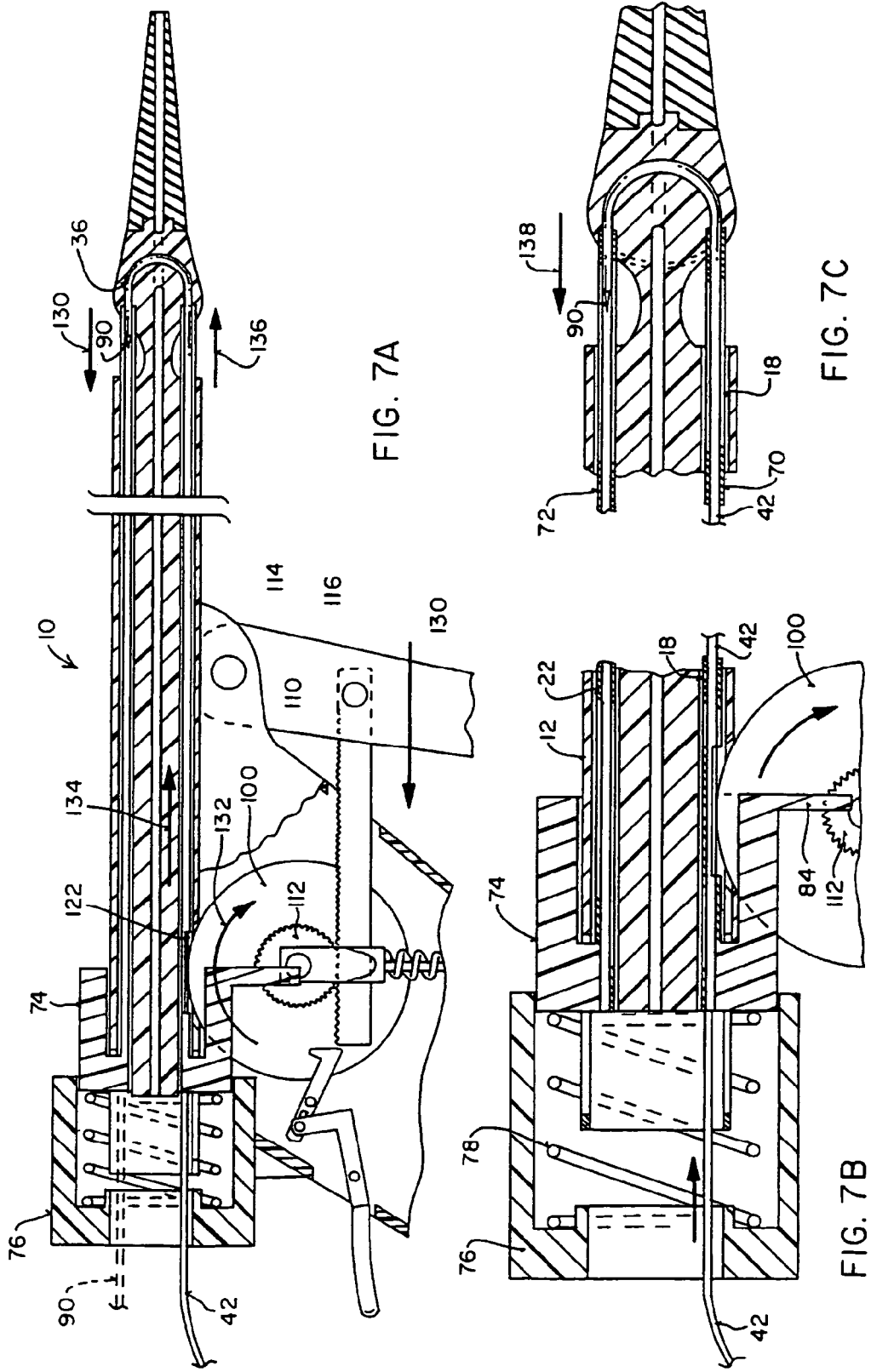

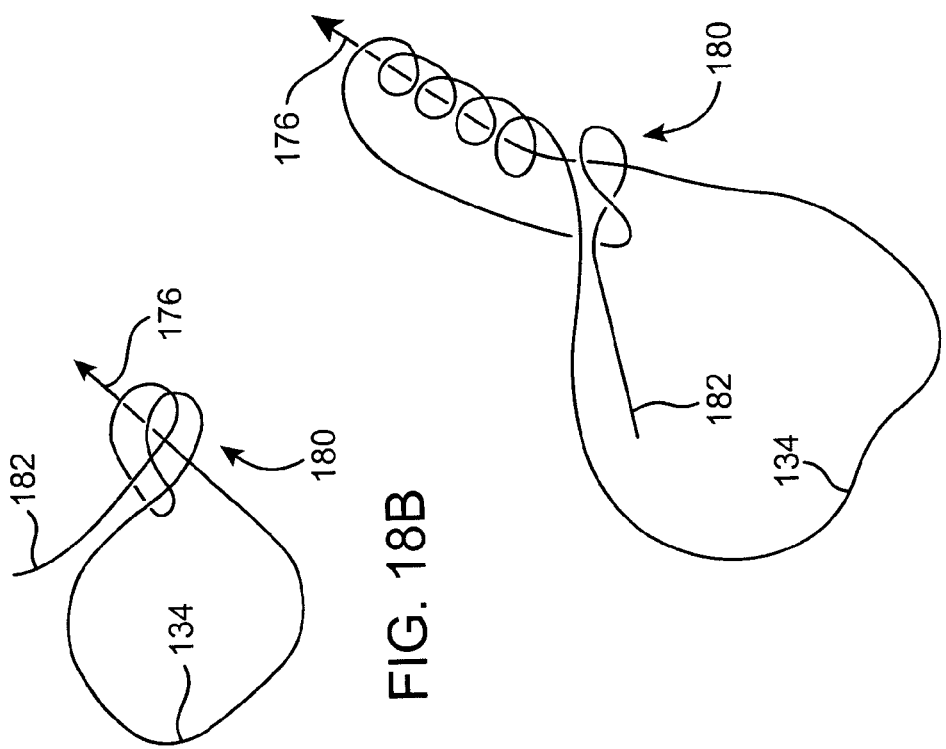

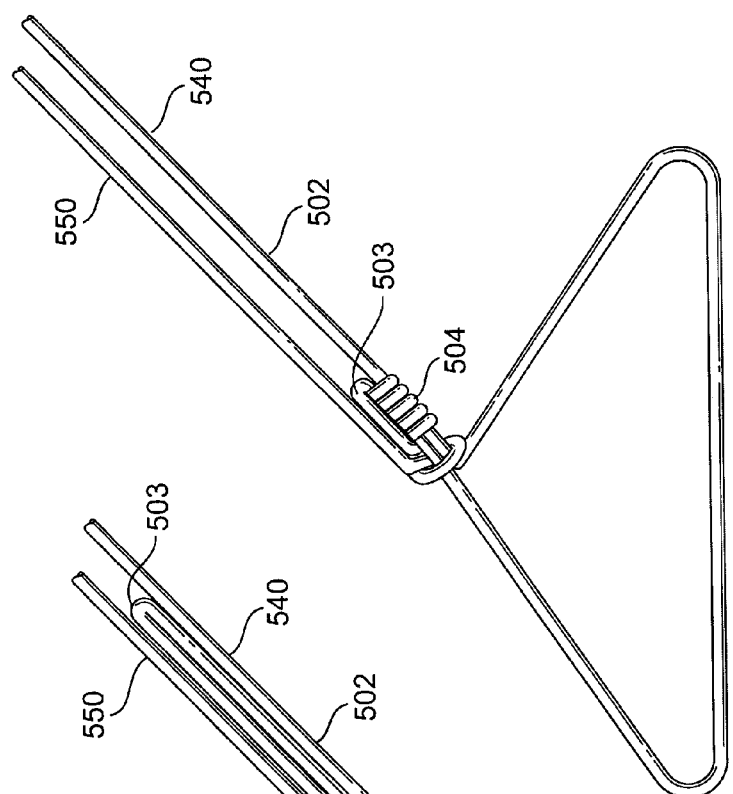
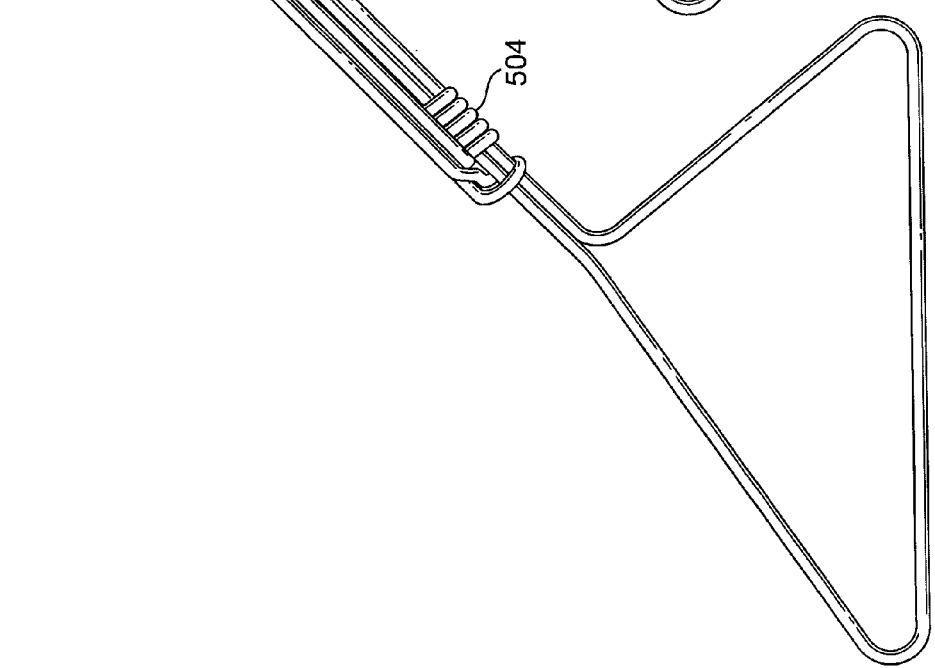

DEVICE AND METHOD FOR SUTURING OF INTERNAL PUNCTURE SITES

RELATED APPLICATION

This application is related to U.S. application Ser. No. 10/335,065, filed Dec. 30, 2000; U.S. Pat. Nos. 6,517,553; 6,206,893; 5,792,152; and 5,527,322, the disclosures of which are incorporated by reference.

BACKGROUND OF THE INVENTION

1. Field of the Invention

The present invention relates generally to devices and methods for the percutaneous closure of body lumens. More particularly, the present invention relates to devices and methods for the percutaneous closure of arterial and venous puncture sites, which are usually accessible only through a tissue tract.

A number of diagnostic and interventional vascular procedures are now performed transluminally, where a catheter is introduced to the vascular system at a convenient access location and guided through the vascular system to a target location using established techniques. Such procedures require vascular access which is usually established using an introducer sheath according to the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach for achieving hemostasis (the cessation of bleeding) is to apply external force adjacent to and upstream from the puncture site, typically by manual or "digital" compression. This approach suffers from a number of disadvantages. It is time-consuming, frequently requiring one-half hour or more of compression before hemostasis is assured. It is uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least six and at times as long as eighteen hours under close observation to assure continued hemostasis. During this time renewed bleeding may occur resulting in bleeding through the tract, hematoma, and/or pseudoaneurism formation as well as arteriovenous fistula formation. These complications may require blood transfusion and/or surgical intervention. The incidence of these complications increases when the sheath size is increased and when the patient is anticoagulated. It is clear that the standard technique for arterial closure can be risky and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

For these reasons, it would be desirable to provide improved devices and methods to close and seal body lumen puncture sites. It would be particularly desirable to provide percutaneous devices and methods for suturing the puncture sites required for percutaneous vascular procedures.

2. Description of the Background Art

Devices capable of delivering needles to various tissue locations are described in the following patents and patent applications: U.S. Pat. Nos. 4,493,323 and 659,422; European patent application 140 557; and U.S.S.R patent applications 1174-036-A and 1093-329-A. Other suturing and ligating devices are described in U.S. Pat. Nos. 3,665,926; 2,959,172; and 2,646,045. Devices for sealing percutaneous vascular penetrations using various plug and fastener structures are described in U.S. Pat. Nos. 5,222,974; 5,192,302; 5,061,274; 5,021,059; 4,929,246; 4,890,612; 4,852,568; 4,744,364; 4,587,969; and 3,939,820. Collagen fastener sealing devices are under commercial development by Datascope Corp., Montvale, N.J., and Kensey Nash Corporation, Exton, Pa. U.S. Pat. No. 4,161,951, describes a needle driver to facilitate surgical suturing. U.S. Pat. No. 4,317,445, discloses a catheter having an axial lumen which provides an indication of blood flow when the catheter has been successfully introduced to the vascular system. A brochure entitled "Innovation Through Progress" published by REMA-Medizintechnik GmbH, Durbheim-Tuttlingen, Germany, describes a suturing device which carries a pair of needles with a length of suture extending therebetween at its distal end. Features of the REMA-Medizintechnik suturing device appear to be described in DE 42 10 724. A device and method for the suturing of vascular penetration sites are described in copending application Ser. No. 07/989,611, commonly assigned with the present application.

SUMMARY OF THE INVENTION

The present invention provides devices and methods for suturing tissue penetrations and puncture sites and is particularly useful for the suturing of puncture sites distal to a tissue tract, such as punctures formed in blood vessels to provide vascular access. Devices according to the present invention will comprise a needle-guiding device including a shaft having a proximal end and a distal end and will define a needle path having an entry segment, a return segment, and an exit segment. Using such devices, elongate flexible needles may be guided through tissue on either side of a puncture site by pushing on the needle from the entry segment. The needle will then pass through tissue captured in a gap or transition region between the entry segment and the return segment. The needle is resiliently flexed (elastically deformed) to turn back on itself as it passes through the return segment of the needle path and is thus directed proximally into the exit segment. The needle thus also passes through tissue captured in the gap between the return segment and the exit segment, permitting suture to be drawn by the needle through opposed sides of the puncture site. The suture may then be tied off to close the puncture in a conventional manner.

According to a first aspect of the method of the present invention, the elongate flexible needle is provided and pushed inwardly so that its distal tip penetrates through an anterior surface of the wall of a body lumen adjacent a puncture site. The flexible needle is then resiliently flexed elastically deformed) as it travels within the interior of the body lumen so that the distal tip will penetrate proximally (outwardly) through a posterior surface of the luminal wall adjacent the puncture site. As it emerges from the device, the needle straightens and may be pulled outwardly to draw suture through the needle penetrations thus formed on opposite sides of the puncture, and the suture tied off to close the puncture site.

According to a second aspect of the method of the present invention, both the elongate flexible needle and a needle-guiding device are provided. The needle-guiding device defines the needle path having an entry segment, a return segment, and an exit segment. The needle-guiding device is first introduced through a tissue tract so that a gap between the entry/exit segments and the return segment lies at the puncture site. After the needle-guiding device is in place, the flexible needle may be pushed through the entry segment of the needle path so that the needle first passes through tissue adjacent the puncture site and into the return segment of the needle path. The needle is then turned as it advances through the return segment so that it passes outwardly through tissue on the other side of the puncture site and then into the exit segment. The needle is pushed sufficiently far so that the distal end of the needle emerges from the exit segment of the needle path where it may be manually grasped and pulled from the needle-guiding device. The suture is then released from the device, the device withdrawn, and the suture tied to close the puncture site.

In a first aspect of the device of the present invention, the suturing device comprises a needle-guiding device including a shaft having a proximal end, a distal end, an entry lumen, and an exit lumen. A nose piece is attached to the distal end of the shaft and includes a return lumen disposed to receive the flexible needle from the entry lumen and to turn the needle to enter the exit lumen as the needle is advanced from the entry lumen. A gap between the shaft and the nose piece receives the tissue to be sutured and exposes the tissue to passage of the suturing needle.

Typically, the nose piece will be elongated with a tapered distal tip and will have a circular cross-section having a maximum peripheral length which is generally equal to that of a transition region which defines a tissue-receiving gap between the nose piece and the shaft. In a preferred embodiment, the nose piece will be fixed relative to the shaft. In an alternate embodiment, the nose piece will be rotatable relative to the shaft. In either case, it will be necessary for the nose piece to align the entry and exit ports of the return lumen to receive the needle from the entry lumen and direct the needle to the exit lumen.

In another aspect of the device of the present invention, guide tubes are provided together with a mechanism to selectively extend the guide tubes across the tissue-receiving gap between the entry lumen and the entry port of the return lumen and between the exit port of the return lumen and the exit lumen. The needle guide tubes help assure that the flexible needles will not become misaligned during passage through tissue across the gap between the shaft and the nose piece.

In another particular aspect of the present invention, the device further comprises a drive wheel on the shaft disposed to engage a flexible needle present in the entry lumen. In this way, even very flexible needles (lacking substantial column strength) can be advanced through the entry lumen to the return lumen and subsequently to exit lumen. The present invention still further provides a suturing kit including a needle-guiding device, as described above, in combination with a flexible needle attached to a length of suture. The needle will have a length sufficient to permit its introduction through the entry lumen, return lumen, and exit lumen, so that the needle may be advanced by pushing on the needle within the entry lumen until a distal end of the needle emerges from the exit lumen. In this way, a user can advance the needle entirely through the needle-guiding path, and grasp the needle once it is emerged from the exit lumen, either manually or using hemostats. Preferably, the needle will be from 10 cm to 30 cm in length. The needle may then be withdrawn from the needle-guiding device and the suture released from the device. After the device is withdrawn from the tissue tract, the suture may be tied off in a conventional manner.

The present invention further comprises kits including the needle guiding device, the needle, and suture. Conveniently, all three components can be packaged together in sterile packaging, such as a sterile flexible pouch.

The devices and methods of the present invention are useful wherever it is desired to place a tied suture loop to close a tissue puncture site, particularly a puncture site through the wall of a body lumen, and more particularly a percutaneous vascular puncture site at the distal end of a tissue tract. The devices and methods can achieve closure wholly within the tissue tract leading to a puncture site and can be manipulated entirely from the portion of the device lying outside of the tissue tract. The present invention will find its greatest use in the sealing of a femoral artery cannulation site made in connection with percutaneous transluminal procedures such as angiography, angioplasty, atherectomy, laser ablation, stent placement, intravascular drug delivery, intravascular imaging, and the like. The present invention will also find use in other medical procedures which rely on percutaneous access to hollow body organs and lumens, such as laparoscopic procedures, endoscopic procedures, artheroscopic procedures, and the like.

The present invention also provides a method of closing a puncture in a blood vessel wall by: positioning a suture placement device through the puncture in the blood vessel wall, the placement device having a length of suture with a first end, a second end and a bight between the first and second ends with the bight being prearranged on the device to define a pre-tied knot when the first end of the suture passes through the bight; advancing the first end of the length of suture in a distal direction from the device through a first penetration in the blood vessel wall adjacent to the puncture; guiding the suture length from the first penetration across a proximal side of the puncture to a second penetration adjacent to the puncture opposite the first penetration; and advancing the suture length in a proximal direction through the second penetration, through the device, and through the bight so that the two ends of the suture length are accessible for securing the suture across the puncture to close the puncture.

The length of suture may be advanced in a distal direction by pushing a needle which carries the suture through the first penetration. Guiding the suture length may be accomplished by elastically bending the needle as it tracks within the blood vessel to the second penetration. Advancing the suture length in a proximal direction may be accomplished by pushing the needle so that a needle tip passes proximally out through the vessel wall adjacent the puncture.

BRIEF DESCRIPTION OF THE DRAWINGS

FIG. 1A illustrates a flexible suturing needle attached to a length of suture, which needle and suture may be introduced using the suturing device of FIG. 1.

FIG. 1B illustrates an alternative distal end configuration for the suturing device of FIG. 1.

FIG. 3 is a detailed view of the distal end of the suturing device of FIG. 1, with portions broken away.

FIG. 3A is a cross-sectional view taken along line 3A-3A of FIG. 3.

FIG. 3B is a cross-sectional view taken along line 3B-3B of FIG. 3.

FIGS. 5A-5C illustrate the suturing device in its initial configuration prior to extension of needle guide tubes and advancement of a suturing needle.

FIGS. 6A-6C illustrate the suturing device in an intermediate configuration after the needle guide tubes have been advanced but prior to advancement of the suturing needle within the needle guide path.

FIGS. 7A-7C illustrate the suturing device with the needle guide tubes advanced and the suturing needle partially advanced through the needle guide path by a needle drive wheel.

FIGS. 18A and 18B are illustrations of a bight of suture arranged in a square knot and a clinch knot, respectively.

FIGS. 19A and 19B are schematic views of a suture bight having a pre-tied knot in accordance with one embodiment of the present invention.

DESCRIPTION OF SPECIFIC EMBODIMENTS

Figure 1:
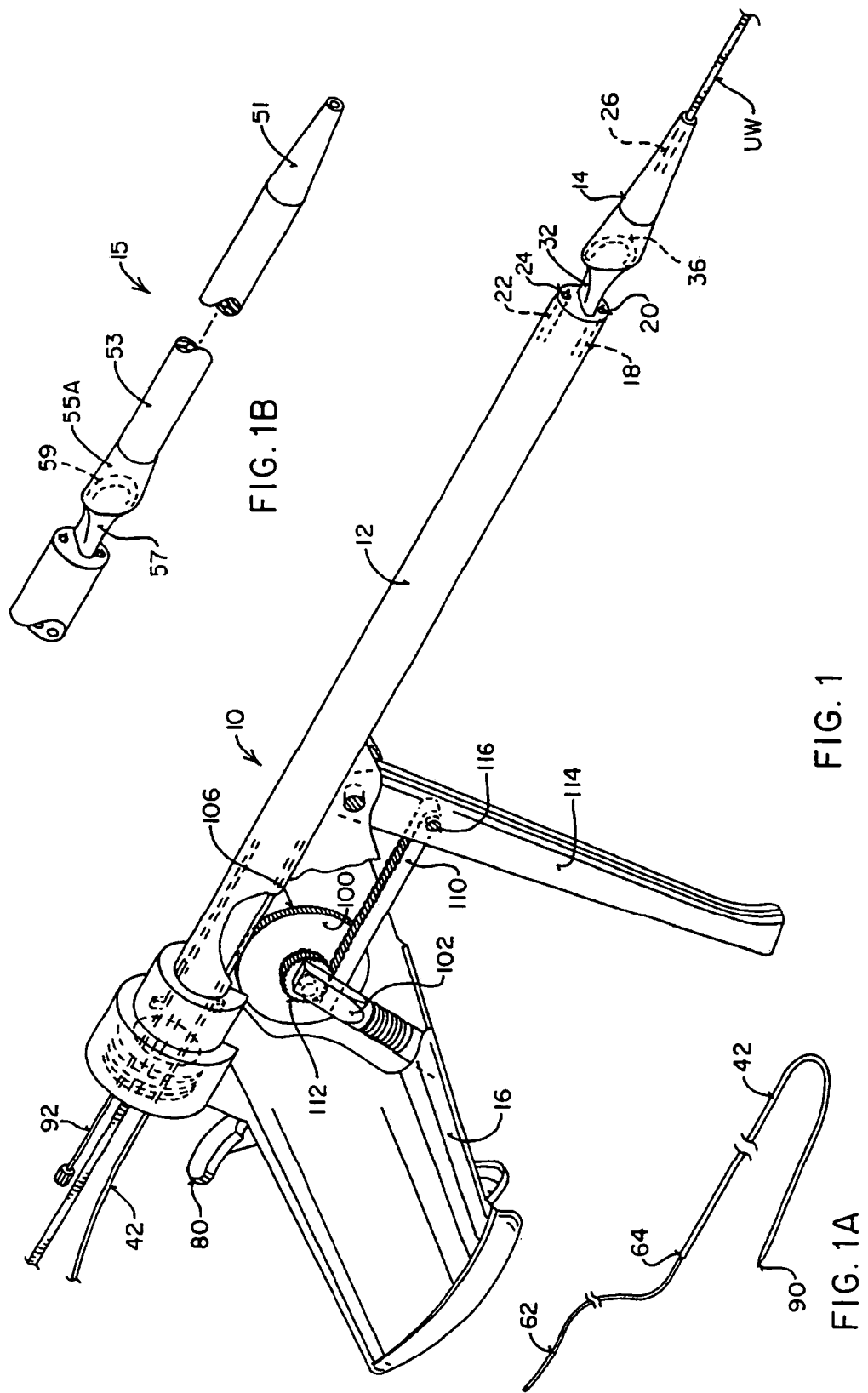
FIG. 1 is a perspective view of a suturing device constructed in accordance with the principles of the present invention.

Referring now to FIGS. 1-3, 3A, and 3B, a suture applying device 10 which is suitable for suturing and sealing of a percutaneous vascular puncture site, particularly punctures made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate a different usage environment.

The suture applying device 10 of the present invention comprises an elongate shaft 12 having a nose piece 14 at its distal end and a handle 16 at its proximal end. The shaft is illustrated as an elongate cylindrical rod having a plurality of axial lumens formed therein, but could also comprise a variety of other geometries which are able to fulfill the essential requirements of the shaft, i.e., defining a needle guide path from its proximal end to its distal end and again back from the distal end to the proximal end. The shaft will usually also include or otherwise define a guide wire lumen (particularly for vascular applications), and a blood pressure detection lumen. Each of these aspects will be described in more detail with regard to the exemplary embodiment of FIGS. 1-3.

Shaft 12 includes a needle entry lumen 18 terminating at a needle exit port 20 at its distal end and a needle exit lumen 22 which begins with a needle entry port 24 at its distal end. The shaft 12 further includes a guide wire lumen 26 which extends through the nose piece 14 and a blood pressure detection lumen 28 having a blood inlet port 30 at its distal end. The blood inlet port 30 is located within a transition gap-defining region 32 between the nose piece 14 and shaft 12, as will be described in more detail hereinafter.

The nose piece 14 includes a needle return lumen 36 which is preferably a U-shaped lumen having a needle entry port 38 aligned with needle exit port 20 of the needle entry lumen 18 and a needle exit port 40 aligned with needle entry port 24 of the needle exit lumen 22. In this way, a flexible needle 42 (FIGS. 1A and 3) entering through the entry lumen 18 will be able to pass across the gap defined by the transition region 32 and into the needle return lumen 36 (in some cases through a needle guide tube as described in connection with FIG. 3 hereinafter) where its direction of travel will be reversed from the distal direction to the proximal direction. The needle 42 will then emerge from the needle exit port 40 of return lumen 36 and be able to enter the needle exit lumen 22 through aligned needle entry port 24. Thus, tissue disposed in transition region 32, i.e., the gap between the distal end of shaft 12 and the proximal end of nose piece 14, will be penetrated by the flexible needle 42 on opposite sides of a puncture site, as will be described in greater detail hereinafter.

In the suturing of a puncture site in the wall of a body lumen, and in particular the wall of a blood vessel, it is desirable to minimize and preferably eliminate any tearing or enlarging of the puncture during the suturing procedure. With the device of the present invention, however, it will also be desirable to distend the periphery of the puncture so that its edges are extended along an axis transverse to that of the blood vessel. In this way, opposed edges of the puncture will be exposed to the needle as it passes through the transition region 32 between the nose piece 14 and the shaft 12. In order to simultaneously achieve both these objectives, i.e., distending the edges of the puncture, without tearing, and further provide a nose piece 14 having sufficient size to space the entry and exit ports of the return lumen 36 sufficiently far apart to be aligned with needle ports 20 and 24, the geometry of the nose piece 14 and of the transition region 32 are selected to properly configure and conform the edges of the luminal puncture as the suture applying device 10 is introduced therethrough.

In particular, the nose piece 14 will be tapered from a small-diameter generally circular distal tip 50 to a proximal portion or length 52 having a generally oval configuration, as best illustrated in FIGS. 3 and 3A. In the illustrated embodiment, the nose piece 14 is generally conical until a circular junction 53 is reached. The proximal portion 52 of the tip makes a transition from a circular cross-section at 53 to an oval cross-section at 55. The particular dimensions of the tip will be selected based on the intended use of the device 10. For the suturing and sealing of the femoral artery, the distal tip 50 will typically have a diameter from about 0.25 mm to 1 mm, typically being just large enough to receive the guide wire GW into the guide wire lumen 26. The maximum dimensions of the oval-shaped proximal portion at 55 will be in the range from 2 mm to 4.5 mm (major diameter) and in the range from 1 mm to 2.25 mm (minor diameter). In particular the major diameter will be selected to permit the needle entry port 38 to be sufficiently spaced-apart from the needle exit port 40 to provide a desired distance between the entry and exit penetrations of the suturing needle through the tissue surrounding the luminal puncture. The oval cross-section of the proximal end 55 of the proximal portion 52 is thus desirable since it minimizes the total peripheral length about the nose piece 14 which must pass through the luminal wall puncture while maximizing the distance between the entry port 38 and exit port 40, as just described. In this way, proper spacing of the needle passages through the tissue will be provided with minimum stretching or enlargement of the luminal penetration.

Figure 2:
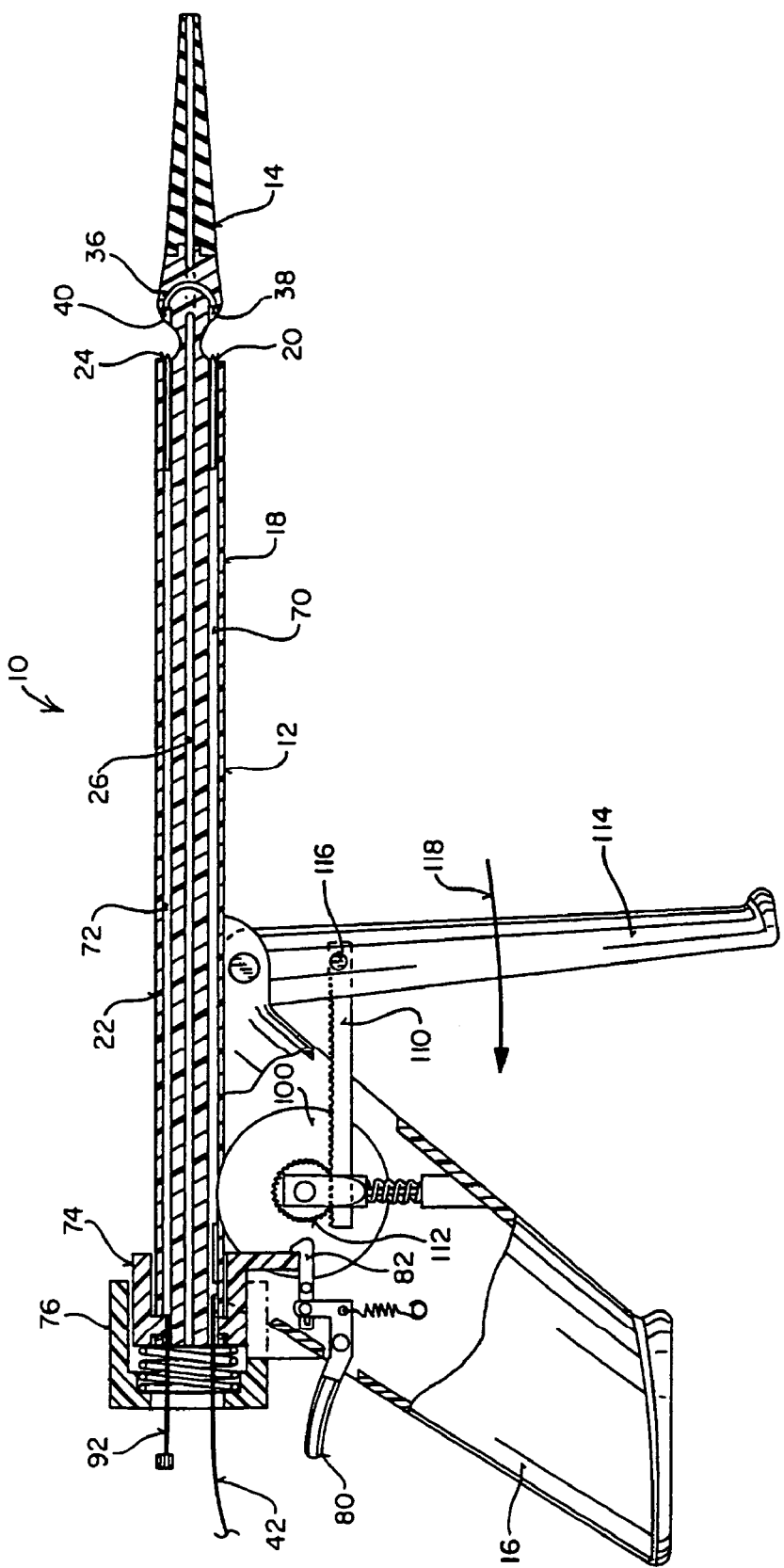
FIG. 2 is an elevation view of the suturing device of FIG. 1, with portions broken away.

The geometry of the transition region 32 will also be chosen to provide for proper manipulation and positioning of the tissue surrounding the luminal puncture site with minimum distending (and preferably no tearing) of the edges of the puncture site. In the embodiment of FIGS. 1-3, the transition region 32 will conform at its distal end to the oval shape of the proximal end 55 of the proximal portion 52 of nose piece 14. The cross-sectional orientation of the transition region 32 changes in the proximal direction, eventually becoming an oval 57 having its major axis disposed orthogonally (i.e. at 90 degrees) relative to the major axis of the proximal portion 52 of nose piece 14 (FIG. 3B). The oval cross-section of the transition region 32 will rotate 90 degrees from the position at 55 to the position at 57. That is, the peripheral shape and distance will remain constant, but the orientation of the major axis will turn through 90 degrees over the axial length of the transition region. By maintaining a constant total peripheral length around the transition region at all points (e.g., equal to the outer diameter of the introducer sheath which had been used in performing the intravascular procedure and removed prior to suturing), the luminal penetration is held firmly and turned to the desired orientation without further distending or tearing.

An alternative nose piece 15 configuration for the suturing device 10 is illustrated in FIG. 1B. The nose piece 15 comprises a tapered distal tip 51, a generally cylindrical shank portion 53, and a proximal portion 55A (which is similar to the proximal portion 52 of the previous embodiment). A needle return lumen 59 is formed in the proximal portion 55A and is generally identical to the lumen 36 described above. The nose piece 15 will be longer than the nose piece 14, typically having a length in the range from 15 cm to 30 cm, usually about 20 cm. The purpose of the longer nose piece 15 is to allow the suturing device 10 to be partially withdrawn from the luminal puncture. By partially withdrawing the device 10, the suture can be released from the nose piece, and the suture partly tightened prior to total withdrawal of the device 10. In this way, the puncture can be at least partly closed by the suture prior to removal of the device, and hemostasis can be maintained to limit blood loss prior to complete closure of the puncture.

Usually, both the tapered distal tip 51 and the shank 53 will have circular cross-sections, with the peripheral length of the shank being uniform along its length and generally equal to the maximum peripheral length of the nose piece 15, usually having a diameter equal to that of the introducer sheath which had previously been in place in the puncture. The proximal end portion 55 serves as a transition from the circular peripheral shape of the shank 53 to an oval transition region 57, which will generally be identical to the transition region 32 in device 10.

The remaining description herein will refer specifically to device 10 having the nose piece 14 illustrated in FIGS. 1, 2, 3, et seq, but it will be appreciated that such description applies as well to devices incorporating nose piece 15.

The suturing needle 42 and attached suture 62 are illustrated in detail in FIG. 1A. Suturing needle 42 will be formed from a highly flexible material which will be able to pass through the radius of return lumen 36. Typically, the turn radius will be in the range from about 1 mm to 2.25 mm, and the needle 42 will have to be able to pass through this radius without undergoing substantial permanent (non-elastic) deformation which would cause binding or jamming as the needle passes outward from the return lumen 36. Preferably, the needle 42 will be formed from stainless spring steel or a superelastic material, typically nickel titanium alloy. Preferred superelastic nickel titanium alloys are available commercially from suppliers, such as Shape Memory Applications, Sunnyvale; Calif., Innovative Technologies International, Beltsville, Md. and Fort Wayne Metals, Fort Wayne, Ind. The diameter of the needle will typically be from about 0.2 to 0.5 mm, and the length will be sufficient to permit the needle to be advanced through the entry lumen 18, across the return lumen 36, and outward through the exit lumen 22, while the needle is being pushed from a location at or near the proximal end of the entry lumen 18. Typically, the needle will have a length in the range from about 10 cm to 30 cm, preferably in the range from about 15 cm to 20 cm. The needle will be attached to a length of suture, typically from about 50 cm to 100 cm, usually at the proximal end of the needle. Particular methods for forming needles and attaching needles to suture are well known in the art.

Figures 4A, 4B:
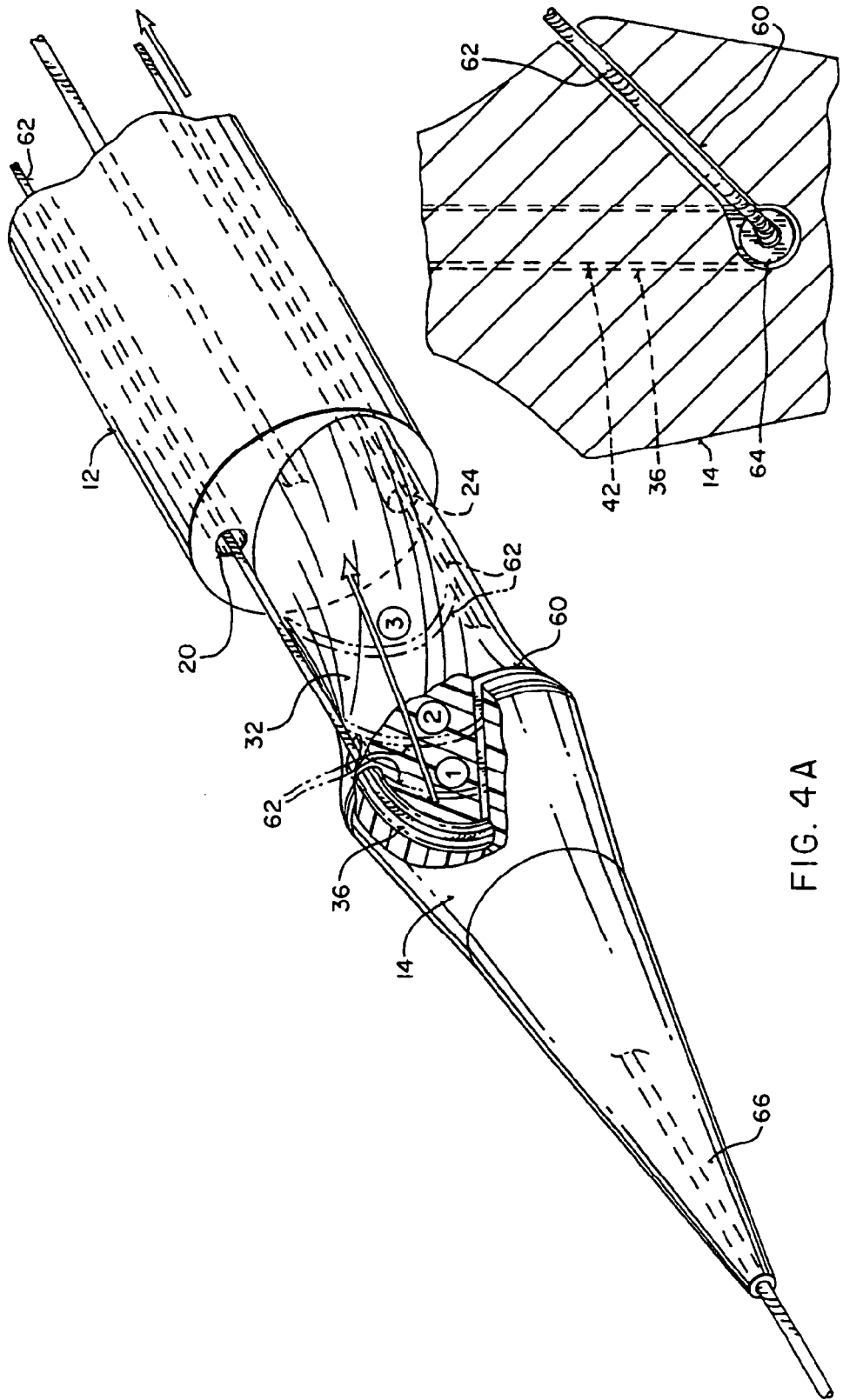
FIG. 4A is a detailed view similar to FIG. 3, illustrating the release of suture from the distal end of the device.
FIG. 4B is a cross-sectional detail of FIG. 4A illustrating a suture-release slot of the present invention.

Referring now to FIGS. 4A and 4B, in a preferred embodiment of the present invention, suture 62 (FIG. 1A) will be released from the nose piece 14 through a suture-release slot 60. The needle return lumen 36 in nose piece 14 will have a diameter which is large enough to receive the flexible needle 42 with a clearance in the range from 0.03 mm to 0.1 mm. The width of the suture-release slot 60, however, will be less than the diameter of the flexible needle 42, typically from 0.1 mm to 0.35 mm. In this way, the needle 42 will travel through the return lumen 36 and will not be able to escape through the suture-release slot 60. Suture 62 which is attached to the butt end of the flexible needle 42 will be sufficiently small to pass through the suture-release slot 60. Thus, after the needle 42 has passed entirely through the needle return lumen 36 and into the needle exit lumen 22 in shaft 12, the suture 62 will pass out of the nose piece 14 through the suture release slot 60, as illustrated in steps (1), (2), and (3) in FIG. 4A. The suture 62 will thus directly engage the posterior side of the tissue to be sutured, leaving the nose piece 14 free to be withdrawn through the luminal puncture without entanglement with the suture 62. FIG. 4B illustrates a proximal or trailing end 64 of the flexible needle 42 as it passes through the needle return lumen 36. As can be seen, the suture 62 passes into the suture-release slot 60 as it is drawn through the return lumen 36 by the needle 42. Alternative suture-release mechanisms will be described in connection with FIGS. 16A, 16B, 17A, and 17B, hereinafter.

In a preferred aspect of the present invention, the nose piece 14 will include a soft tip 66 to facilitate entry into the body lumen being sutured. Conveniently, the soft tip 66 can be formed from a soft polymer, such as a polyether block amide, e.g., Pebax.RTM. The soft tip 66 can be joined to the more rigid proximal portion of the nose piece 14 by any conventional manner. In all other ways, the soft tip 66 can form a continuous structure with the proximal portion of the nose piece 14. The proximal portion of nose piece 14, the transition region 32, and the shaft 12, will typically be formed from a relatively rigid polymer (e.g., polycarbonate) or a metal (e.g., stainless steel) by conventional methodologies, such as extrusion, molding, machining and the like. The different portions of the device may be formed in separate pieces, and joined later, e.g. by the use of adhesives, heat bonding, mechanical attachment or the like.

Referring now to FIGS. 1, 2, and 5A-5C, a needle guide and advancement mechanism constructed in accordance with the principles of the present invention will be described. The needle guide and advancement mechanism includes an entry guide tube 70 and an exit guide tube 72, each being secured at its proximal end in a guide tube yoke 74. The guide tubes 70 and 72 are slidably received in the needle entry lumen 18 and needle exit lumen 22, respectively, so that axial translation of the guide tube yoke 74 (as described hereinafter) can advance the distal ends of the guide tubes across the gap defined by the transition region 32 (as illustrated in FIG. 3 and described in more detail in connection with FIGS. 6A-6C). The guide tube yoke 74, in turn, is slidably mounted in a spring retainer 76, with a spring 78 being disposed therebetween. As illustrated in FIGS. 5A and 5B, spring 78 is in compression, with the entire assembly of the guide tubes 70 and 72 and guide tube yoke 74 being in a retracted configuration, i.e. fully to the left in FIGS. 5A and 5B.

A yoke-release mechanism comprises a thumb lever 80 extending from handle 16 and a latch member 82 which captures the guide tube yoke 74 through an extension 84. The thumb lever 80 and latch member 82 are pivotally mounted within the handle 16 and are operatively connected through a pin and slot 86 so that depression of thumb lever 80 in the direction of arrow 88 will release the guide tube yoke extension 84, as illustrated in FIGS. 6A-6C. In this way, spring 78 will decompress to translate the guide tube yoke 74 distally, i.e. toward the right, as illustrated in FIGS. 6A-6C.

The entry guide tube 70 will carry the flexible suture needle 42 with a sharpened distal tip 90 projecting just out of the distal end of the tube, as illustrated in FIGS. 5A and 5C. In this way, the needle 42 will fill the lumen of the guide tube 70 and prevent tissue from entering the lumen as the guide tube is advanced. The exit guide tube 72 will have a stylet 92 (or other obturator) filling its axial lumen. As illustrated in FIGS. 5A and 5C, the stylet 92 will preferably also have a sharpened distal tip 94 which projects outwardly from the distal end of the guide tube as the guide tube is advanced. The purpose of the stylet 92 is to prevent tissue from entering (and blocking) lumen of guide tube 72 as it is advanced through the tissue. After the exit guide tube 72 has been advanced across the transition region 32, the stylet 92 will be withdrawn leaving the lumen of the guide tube open and available for advancement and passage of the flexible needle 42, as will be described in greater detail in connection with FIGS. 7A-7C.

Referring now in particular to FIGS. 1, 2, and 5A-5C, the exemplary needle guide and advancement mechanism for use with the device of the present invention further comprises a drive wheel 100 rotatably mounted in yoke 102. The yoke 102, in turn, is attached to the interior of handle 16 on a spring mount 104. Spring mount 104 urges the drive wheel 100 against flexible suture needle 42 in a manner described more fully in connection with FIGS. 6A-6C. Preferably, the periphery 106 of the drive wheel 100 is serrated or otherwise roughened to enhance frictional coupling between the drive wheel 100 and the needle 42 to facilitate advancement.

Drive wheel 100 is driven by a rack 110 which engages pinion gear 112 which is coaxially mounted and attached to the drive wheel 100. The rack 110, in turn, is actuated by a lever 114 which is pivotally attached to the handle 16. A mechanism (not illustrated) will usually be provided for biasing the rack 110 against the pinion gear 112. For example, a leaf spring could be provided within the yoke to upwardly bias the rack 110 against the pinion gear 112. Alternatively, a torsion spring could be provided at the pivot 116 connecting the rack 110 to the lever 114.

The drive wheel 100 is actuated by manually squeezing the lever 114 toward the handle 16 in the direction of arrow 118. It will be possible to select the relative diameters of the drive wheel 100 and the pinion gear 112 and the length and pivot point of the rack 110 so that a single stroke of the lever 114 can fully drive the needle through the target tissue, return lumen 36, and needle exit lumen 22, so that the needle can be manually grasped or mechanically captured, e.g., using hemostats, as it emerges from the exit lumen. Alternatively, a mechanism (not illustrated) could be provided to permit multiple, sequential actuation of the lever 114 in order to drive the needle the requisite distance.

The suture applier 10 is illustrated in its "shelf" configuration in FIGS. 2 and 5A-5C. That is, the needle guide tubes 70 and 72 are fully retracted, i.e. drawn to the left in each of these figures. By depressing thumb lever 80, the user releases the guide tube yoke 74, thus driving the guide tubes in the distal-direction as indicated by arrows 120 in FIG. 6A. Such movement of the entry guide tube 70 aligns an elongate cutout 122 in the guide tube with the periphery of drive wheel 100, as best illustrated in FIG. 6B. In this way, the drive wheel 100 directly engages the side of the suture needle 42 which is exposed through the cutout 122. At this moment, the guide tubes will also extend across the transition region 32 and seat into the return lumen 36 in the nose piece 14. The stylet 92 may then be withdrawn in order to open the lumen of the exit guide tube 72 so that it is free to receive the suture needle.

After the stylet 92 is withdrawn, the needle 42 may be advanced by the needle advance mechanism, as illustrated in FIGS. 7A-7C. The lever 114 is manually closed in the direction of arrow 130 to translate rack 110 across the pinion gear 112. This motion causes drive wheel 100 to rotate clockwise in the direction of arrow 132. As the drive wheel 100 is engaging suture needle 42 through the cutout 122, the needle will be moved in the distal direction (arrow 134) causing the sharpened tip 90 to advance and cross the gap defined by transition region (arrow 136), through the return lumen 36 and back through the transition region gap (arrow 138). The needle advancement mechanism will be actuated sufficiently (or for a sufficient number of times) to advance the needle 42 so that its distal end 90 emerges from the proximal end of the device 10, as illustrated in broken line in FIG. 7A. The needle may then be grasped or captured and withdrawn from the device 10 in order to draw the suture through the device and the tissue to be sutured, as will be described in more detail hereinafter.

It would also be possible to modify the drive wheel 100 advance mechanism to engage and advance the guide tube 70 so that the guide tube could be advanced by an initial portion of the stroke of lever 114. Guide tube 70 could be coupled to guide tube 72 through a yoke similar to the yoke 74, but no spring 78 or yoke-release mechanism would be required. A variety of particular mechanisms for advancing the guide tubes and/or needles would be available within the scope of the present invention.

Figure 8:
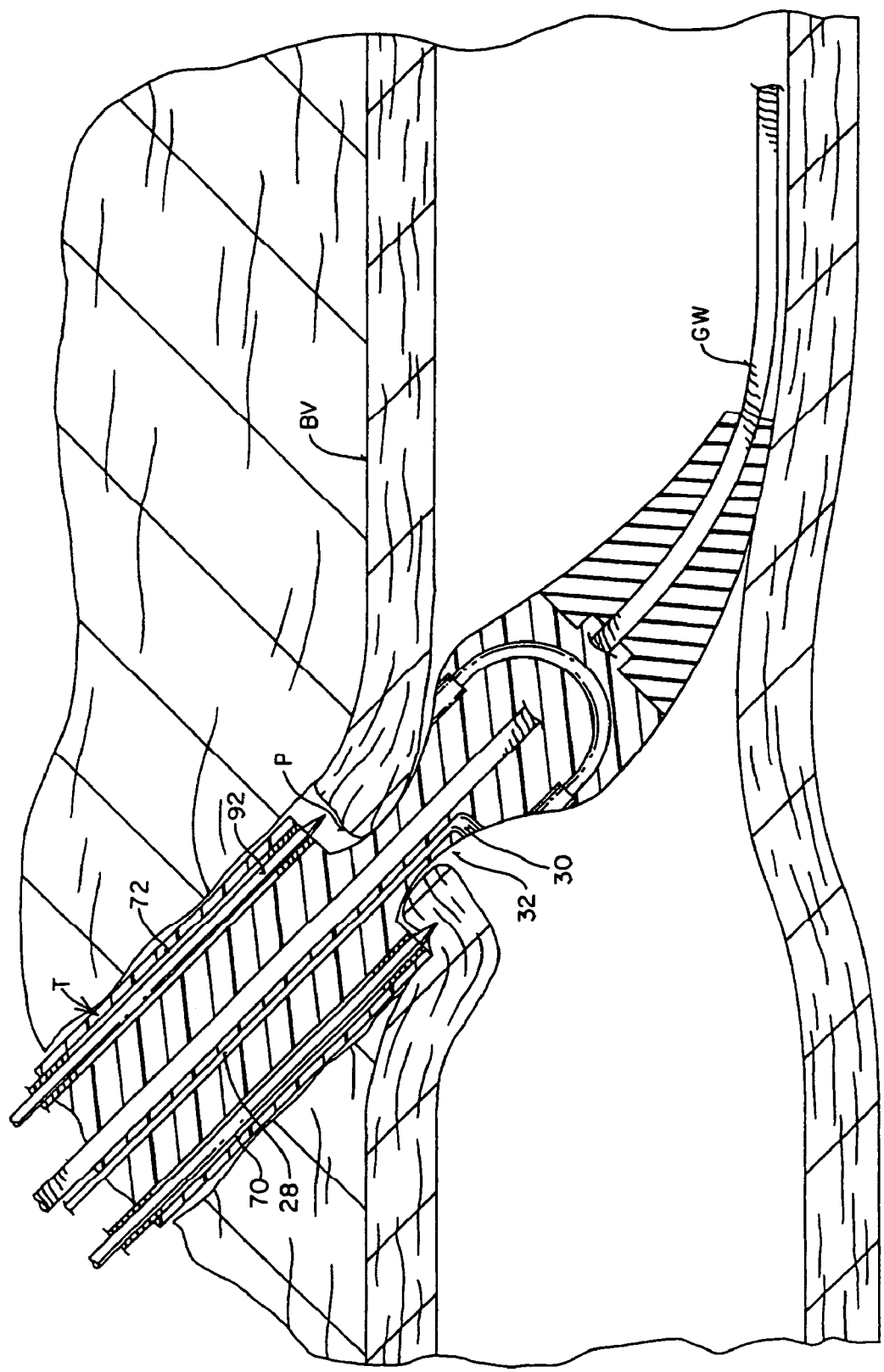
FIG. 8 is a detailed view illustrating the distal end of the needle-guiding device placed within a puncture in the femoral artery prior to advancement of the needle guide tubes.

Referring now to FIGS. 8-13, use of the device 10 for applying end tying a suture loop in a blood vessel BV wall will be described in detail. Referring in particular to FIG. 8, the device 10 is introduced through an existing tissue tract T, typically formed by an introducer sheath which has been previously placed in connection with a conventional intravascular therapeutic or diagnostic procedure, such as angiography, angioplasty, atherectomy, laser ablation, cardiac mapping, cardiac ablation, or the like. The introducer sheath is removed prior to introduction of the nose piece 14 of the suturing device 10. As discussed above, the maximum peripheral length of the nose piece 14 will generally be the same as the circumferential length of the introducer sheath so that the penetration is not torn but remains blocked or occluded by the device to reduce blood loss.

The device 10 is introduced with the needle guide tubes 70 and 72 fully retracted in the proximal direction and with the stylet 92 in place in the lumen of the exit guide tube 72. The device 10 is positioned over the previously placed guide wire GW and introduced sufficiently so that the gap, defined by the transition region 32 receives the edges of the puncture P. Conveniently, proper positioning of the device 10 can be confirmed by detecting the flow of blood into blood inlet port 30 and as it appears at the open proximal end of lumen 28.

Figure 9:
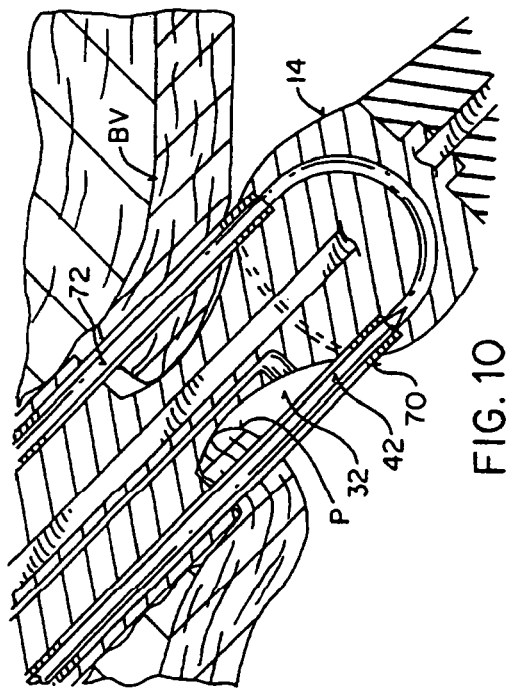
FIGS. 9-12 illustrate successive steps of advancing the suturing needle within the needle-guide path of the needle-guiding device in detail.

After the device 10 has been properly positioned, as illustrated in FIG. 8, the needle guide tubes 70 and 72 will be advanced across the gap defined by the transition region 32, as illustrated in FIG. 9. The needle advancement mechanism, as previously described, will be used to effect the advance. Each guide tube 70 and 72 will pass through tissue which is located within the transition region 32. The presence of the flexible needle 42 in guide tube 70 prevents "coring" of the tissue into the guide tube 70. Similarly, the presence of stylet 92 in needle guide tube 72 prevents such coring.

Figure 10:
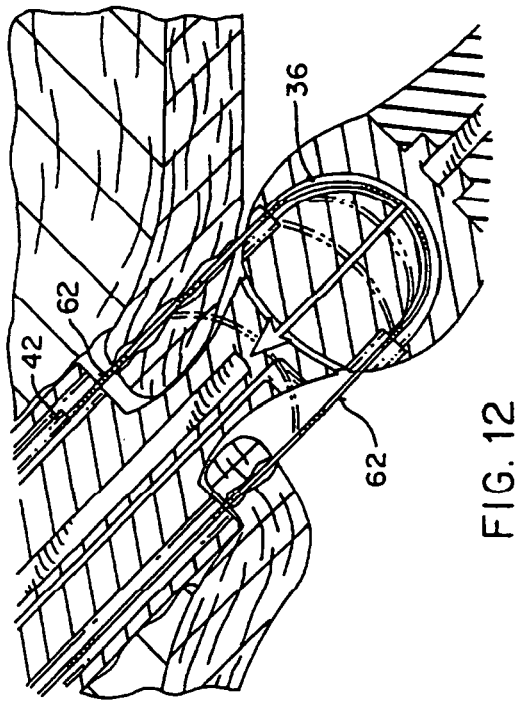

The stylet 92 is next withdrawn, leaving the lumen of the needle guide tube 72 empty and available to receive flexible needle 42, as illustrated in FIG. 10.

Figure 11:
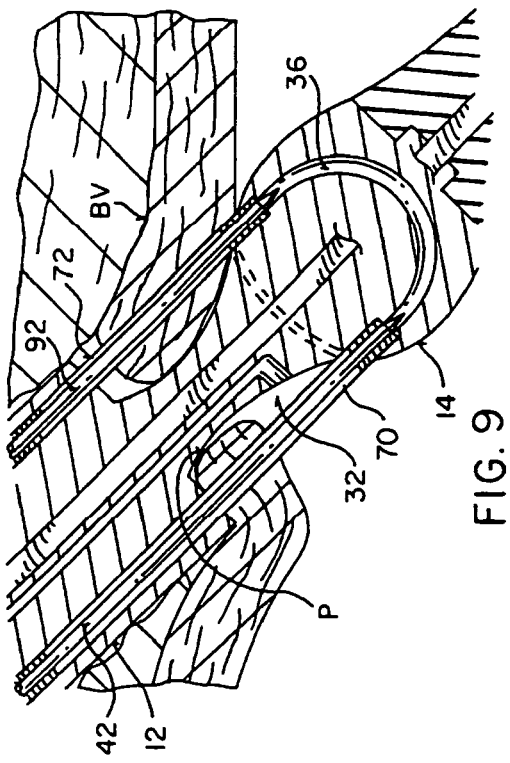
Figure 12:
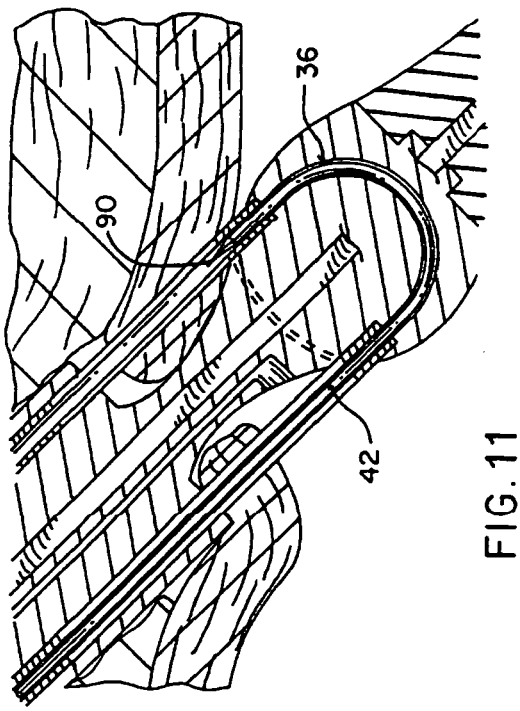
Figure 13:
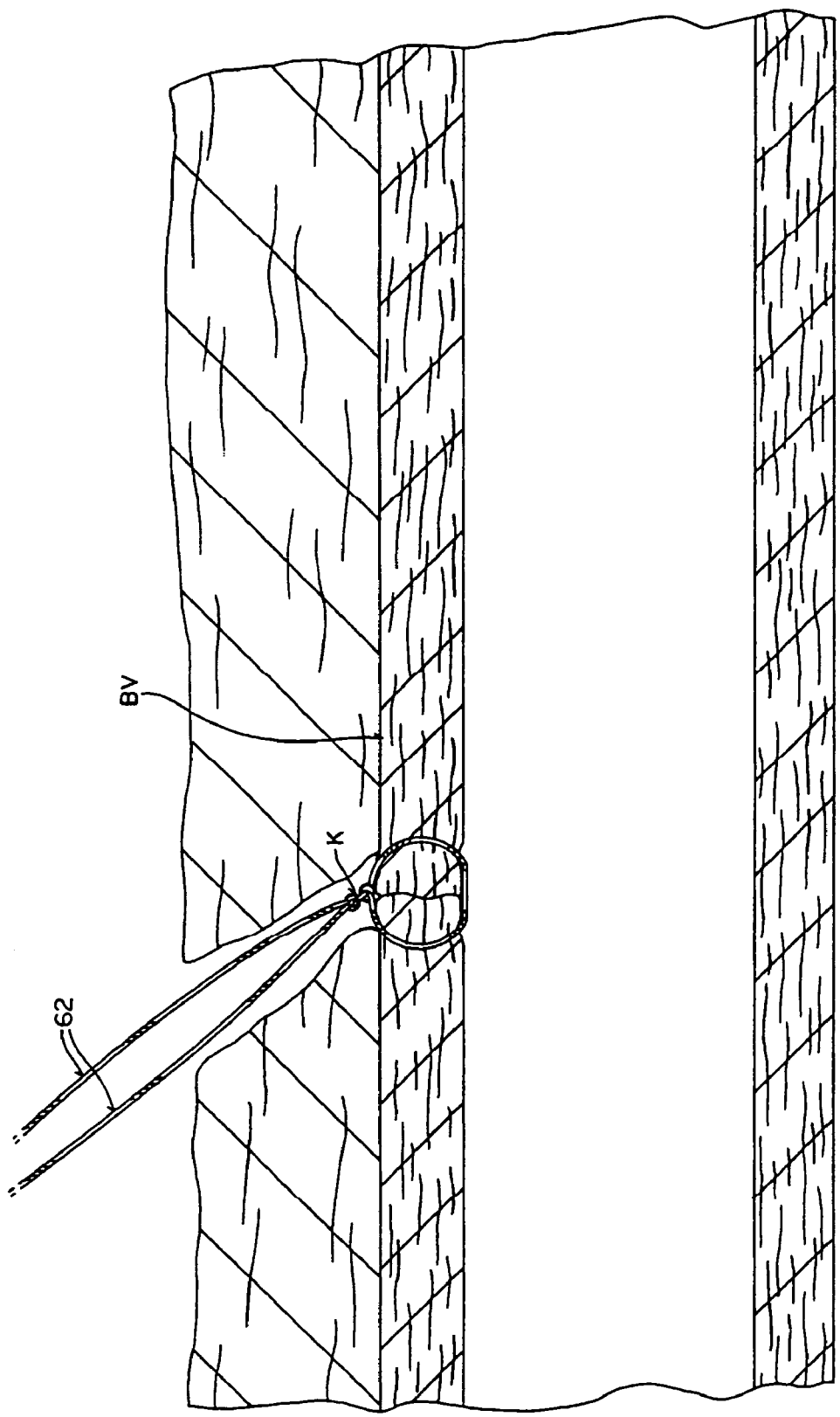
FIG. 13 illustrates a tied suture loop applied by the device in the method of the present invention.

The flexible needle 42 is next advanced across the U-shaped return lumen 36 and into the needle return guide 72, as illustrated in FIG. 11. Note that the highly flexible nature of the needle together with the close fit between the needle 42, guide tubes 70 and 72, and return lumen 32, permits it to turn across the small radius and advance without buckling in spite of the frictional and bending forces opposing the needle's advance. The needle continues to be advanced until the sharpened distal tip 90 emerges from the device 10 (as illustrated previously in FIG. 7A). After it emerges, the needle tip 90 may be grasped and pulled through the device 10, drawing the suture 62 through the return lumen 36. The needle guide tubes 70 and 72 will be withdrawn, permitting the suture 62 to be drawn outward from the nose piece 14 through the suture-release slot 60, as illustrated in FIGS. 4A-4B and 12 (where the outer portion of slot 60 is shown broken away). After the suture 62 has been released from the nose piece 14, the device 10 may be partially or totally withdrawn, leaving the suture accessible for tying of a knot K to close the puncture wound, as illustrated in FIG. 13.

When using a device 10 having an elongated nose piece 15, as illustrated in FIG. 1B, it will be preferred to only partially withdraw the device so that the shank portion 53 remains within the penetration P. As the shank 53 will preferably have a perimeter substantially equal to that of the introducer sheath previously in place, the shank 53 will be able to occlude the puncture to inhibit blood loss, without distending the puncture. The extra length provided by shank 53 permits the nose piece 15 to be withdrawn sufficiently to release the suture 62 while still occluding the penetration P. The knot K can thus be tied and partially tightened prior to total withdrawal of the device 10, allowing very rapid closure of the penetration by tightening the suture.

Figure 14B:
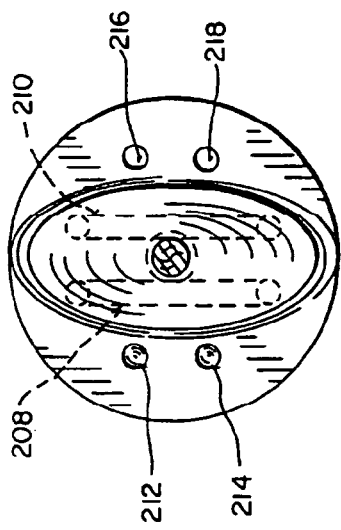
FIGS. 14A-14C illustrate an alternative arrangement of the distal end of the needle-guiding device of the present invention, where a rotatable nose piece carrying a pair of return lumens is provided for receiving a pair of needles from the guide shaft.
Figure 14C:
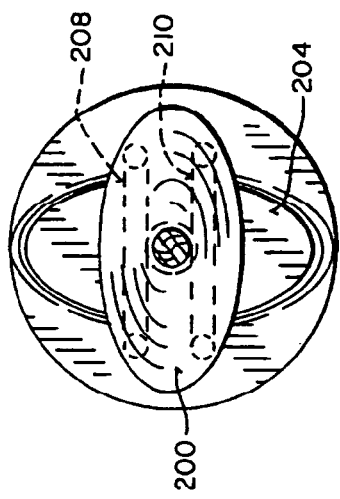
Figure 14A:
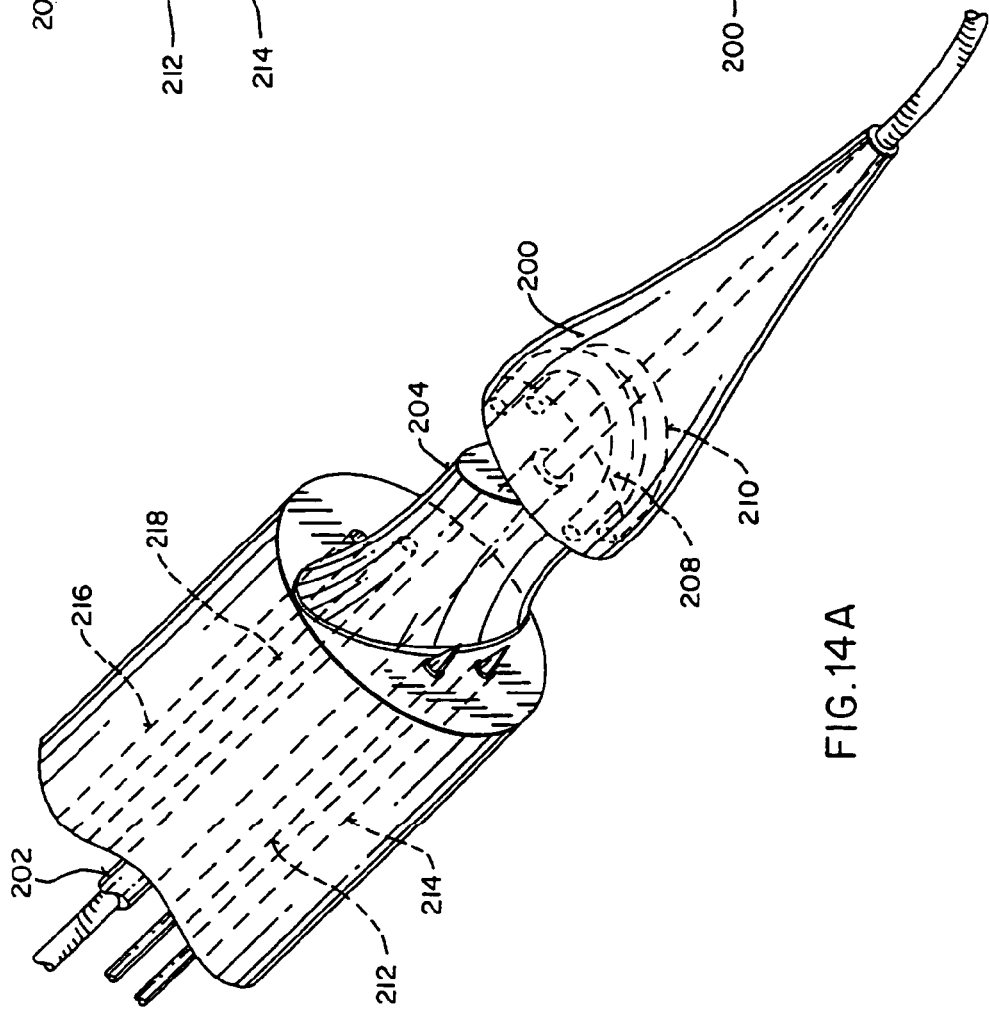

Referring now to FIGS. 14A-14C an alternative embodiment of a nose piece 200 is illustrated. Nose piece 200 is mounted on an axial rod 202 which permits it to be rotated between an aligned position, as illustrated in FIG. 14B, and a transverse position, as illustrated in FIGS. 14A and 14C. When in the aligned position of FIG. 14B, the nose piece 200 has an oval cross-section which gradually increases in size and which forms a smooth and continuous surface with the transition region 204, facilitating introduction of the device through a tissue puncture. The peripheral length of the oval section is matched with the circumference of the introducer sheath used in the initial interventional or diagnostic procedure to minimize distending of the tissue around the luminal puncture site. In the configuration of FIG. 14B, the return lumens 208 and 210, however, are out of rotational alignment with the needle entry lumens 212 and 214 and needle exit lumens 216 and 218. Therefore, prior to needle advancement, the needle entry and exit lumens will be properly aligned with the needle return lumens in the nose piece 200 by rotating the nose piece 200 by 90 degrees to the position of FIGS. 14A and 14C. The nose piece 200 will then be rotated back to the aligned configuration of FIG. 14B after suture release from the nose piece 200 and prior to withdrawal of the device from the tissue tract.

Figure 15A:
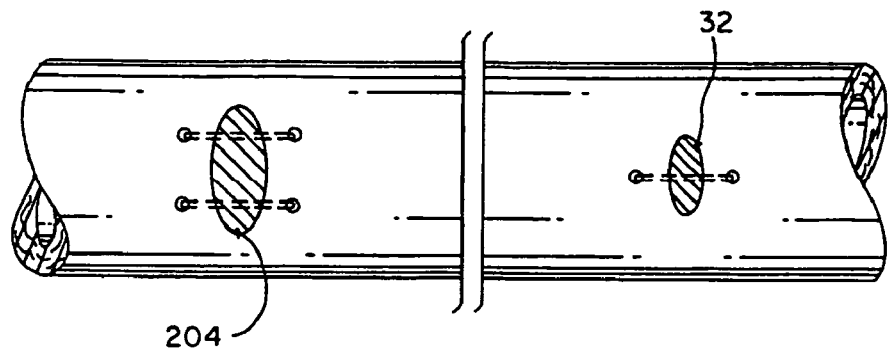
FIGS. 15A and 15B illustrate placement of single and double suture loops using the first and second embodiments of the present invention.
Figure 15B:
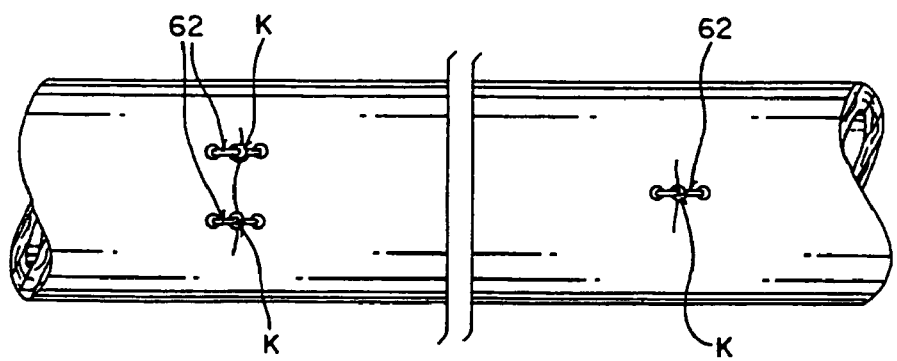

As can be seen in FIGS. 15A and 15B, the embodiment of FIGS. 1-7 can be used to form a single suture loop where the nose piece 14 has a relatively small peripheral length (as illustrated on the right-hand half of each figure). The embodiment of FIGS. 14A-14C is particularly useful for forming pairs of suture loops, as illustrated on the left-hand side of Peach of FIGS. 15A and 15B. Of course, the embodiment of FIGS. 1-7 could be readily adapted to place two sutures simultaneously, while the nose cone of FIGS. 14A-14C could be modified to place only a single suture.

Figure 16A:
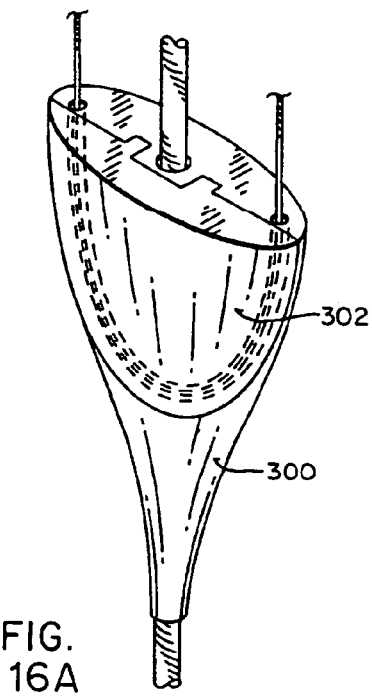
FIGS. 16A and 16B illustrate an alternative suture release mechanism where a portion of the nose piece slides to expose the return lumen.
Figure 16B:
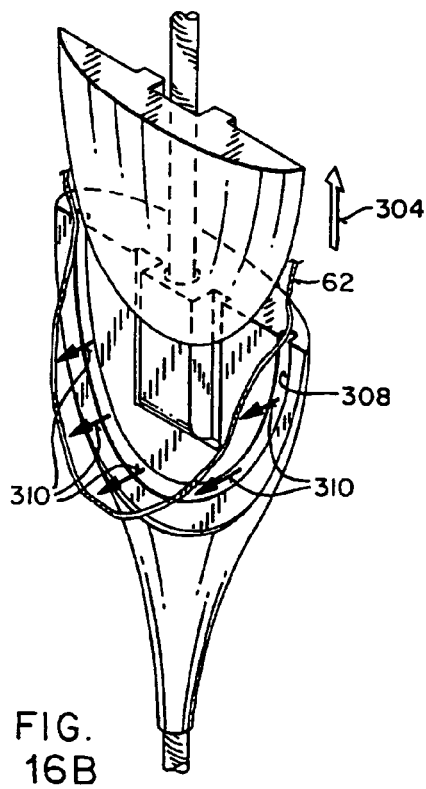

Referring now to FIGS. 16A and 16B, a first alternative suture release mechanism is illustrated. A nose piece 300 includes a sliding cover 302 which may be moved from the covered configuration (FIG. 16A) to the uncovered configuration (FIG. 16B) by sliding the cover proximally, as illustrated by arrow 304. When the cover 302 is moved proximally, return lumen 308 is exposed, permitting the suture 62 to exit from the lumen, as illustrated by arrows 310.

Figure 17A:
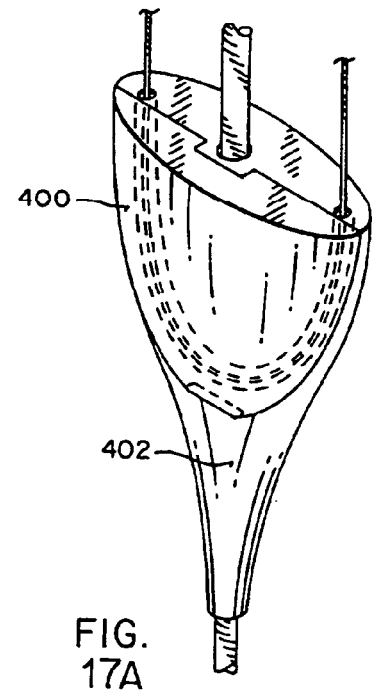
FIGS. 17A and 17B illustrates a second alternative suture release mechanism, where a portion of the nose piece swings open to expose the return lumen and release the suture.
Figure 17B:
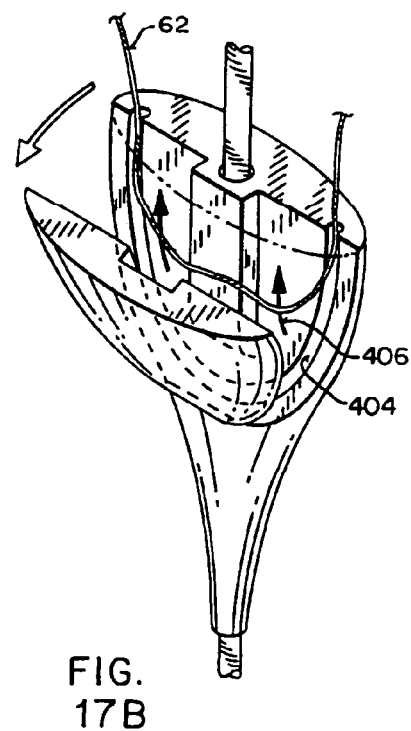

A second suture release mechanism is illustrated in FIGS. 17A and 17B. The mechanism is similar to that illustrated in connection with FIGS. 16A and 16B, except that cover 400 on nose piece 402 is pivotally attached to open as illustrated in FIG. 17B. Suture 62 can thus be released from the return lumen 404, as illustrated by the arrows 406.

Several embodiments of a suturing device that delivers a pre-tied knot to a puncture or incision in a wall of tissue is disclosed. Various aspects of such a device include a length of suture having a bight between first and second ends of the suture. The bight includes one or more loops of suture that form a pre-tied knot when one or more ends of the suture are advanced through the bight. The bight of suture may be pre-arranged in any of several configurations on the device.

As illustrated in FIGS. 18A to 24 the present invention also provides a method of closing a puncture in a blood vessel wall BV by: positioning a suture placement device 10 through the puncture in the blood vessel wall BV, placement device 10 having a length of suture 502 with a first end 540, a second end 550 and a bight 504 between the first and second ends 540 and 550 with bight 502 being prearranged on the device 10 to define a pre-tied knot when the first end 540 of the suture 502 passes through bight 504; advancing the first end 540 of the length of suture 502 in a distal direction from device 10 through a first penetration in the blood vessel wall BV adjacent to the puncture; guiding the suture length 502 from the first penetration across a proximal side of the puncture to a second penetration adjacent to the puncture opposite the first penetration; and advancing the suture length 502 in a proximal direction through the second penetration, through device 10, and through bight 504 so that the two ends 540 and 550 of the suture length 502 are accessible for securing the suture across the puncture to close the puncture.

The present invention also provides a method for suturing a puncture site in a wall of a blood vessel BV, by: providing a suturing device 10 having a pair of axially advanceable penetrating elements 70 and 42 and a length of suture 502 having a first end 540, a second end 550 and a bight 504 between the first and second ends, bight 504 being prearranged on suturing device 10 to define a pre-tied knot when the first end 540 of suture 502 passes through bight 504; advancing the penetrating elements 70 and 42 to form two penetrations in the blood vessel wall on opposite sides of the puncture site; advancing first end 540 of the suture distally through suture device 10, distally through one of the two penetrations into a lumen of the blood vessel, proximally through the other of the two penetrations, proximally through suturing device 10, and through bight 504; and securing the pre-tied knot to close the puncture site.

The penetrating elements may be needle guides (e.g.: 70). Advancing the suture may be done by pushing the suture distally through a lumen of a first needle guide tube (not shown) and pulling the suture proximally through a second needle guide tube 70. Advancing the suture may be accomplished by providing a needle having the suture attached thereto and pushing the needle distally through the lumen of the first needle guide tube (not shown) and pulling the needle proximally through the second needle guide tube 70.

The present invention also provides a method of suturing a puncture site in a wall of a blood vessel BV, by: providing a length of suture 502 having a first end 540, a second end 550 and a bight 504 between the first and second ends, bight 504 being prearranged and adapted to receive the first end 540 therethrough to define a pre-tied knot when the first end 540 of suture 502 passes through bight 504; pushing the suture 502 distally through a tissue tract over the puncture site through a penetration on one side of the puncture site into a lumen of the blood vessel; pulling the suture 502 proximally through a second penetration on another side of the puncture site and proximally through the tissue tract; passing the suture through bight 504; and securing the pre-tied knot to close the puncture site.

The present invention also provides a device 10 for suturing a puncture in a blood vessel wall BV, including: a body 12 arranged to be positioned through a tissue tract over the blood vessel puncture, and a length of suture 502 having a first end 540, a second end 550 and a bight 504 between the first and second ends, bight 504 being prearranged on body 12 to define a pre-tied knot when the first end 540 of the suture 502 passes through bight 504; said body 12 having a suture path for (a) advancing the first end of the suture length in a distal direction past a first gap in the body, (b) advancing the suture laterally on a distal side of the gap, and (c) proximally past a second gap in the body, wherein the gaps are arranged to engage the edges of the blood vessel wall adjacent to the puncture so that the suture advances distally through one edge, laterally across a distal side of the puncture, proximally through the other edge of the blood vessel wall, and through the bight.

In various aspects, body 12 includes a shaft having a nose piece 14, wherein the gaps are positioned between a distal end of the shaft and a proximal surface of nose piece 14. In various aspects, the device further includes a needle 42, needle 42 being configured to carry the suture through the suture path. In various embodiments, the device 10 further comprises a pair of needle guide tubes, said guide tubes arranged to be advanced across the gaps to penetrate the edges of the blood vessel wall to form penetrations prior to advancement of the needle.

The present invention also provides a suturing device 10 including: a shaft having a proximal end, a distal end, an entry lumen, and an exit lumen; a length of suture 502 having a first end 540, a second end 550 and a bight 504 between the first and second ends, bight 504 being prearranged on the shaft to define a pre-tied knot when the first end 540 of the suture 502 passes through bight 504; a nose piece 14 attached to the distal end of the shaft and having a return lumen disposed to receive a flexible needle from the entry lumen and to turn the needle to enter the exit lumen, wherein the nose piece 14 is axially spaced-apart from the distal end of the shaft to form an annular gap between the shaft and a proximal end of nose piece 14 which receives tissue to be sutured.

The present invention also provides a suturing kit including: a suturing needle 42 including an elongate needle shank having a distal tip, said shank being composed of a flexible metal alloy; a length of suture having a first end connected to the needle, a second end and a bight 504 between the first and second ends 540 and 550, the bight 504 being prearranged on body 12 to define a pre-tied knot when the first end of the suture 502 passes through the bight 504; and a suturing device 10 comprising a shaft having a proximal end, a distal end, an entry lumen, and an exit lumen; a nose piece 14 attached to the distal end of the shaft and having a return lumen 36 disposed to receive the flexible needle from the entry lumen and to turn the needle to enter the exit lumen, wherein nose piece 14 is axially spaced-apart from the distal end of the shaft to form an annular gap between the shaft and a proximal end of the nose piece which receives tissue to be sutured.

The present invention may further comprise a transition region having a generally oval cross-section disposed in the gap between the shaft and the nose piece. Furthermore, nose piece 14 may be tapered with an oval cross-section over at least a portion of its proximal length, wherein the maximum peripheral distance around the nose piece 14 at its proximal end is generally equal to that around the transition region. Furthermore, nose piece 14 may include a tapered distal tip, a shank portion having a cylindrical cross-section with a circumference generally equal to the maximum peripheral length, and a proximal end piece which changes to an oval cross-section having a constant peripheral length generally equal to the maximum peripheral length. Needle guide tubes (70 and 72) disposed in the entry and exit lumens (18 and 22) and means to extend the guide tubes across the gap and to the return lumen in the nose piece 14 may also be included. A drive wheel 100 disposed on the shaft to engage a flexible needle present in the entry lumen may be included, whereby rotation of drive wheel 100 advances the needle 42 through the entry lumen 18, across the gap, through the return lumen 36, across the gap, and through the exit lumen 22. The nose piece 14 may have a suture-release slot formed contiguously with the return lumen. Means for opening the nose piece to release suture therefrom may also be included.

Bight 180 will define a knot when first end suture passes therethrough, as can be understood with reference to FIGS. 18A and 18B. Bight 180 is formed from a length of suture 134 having a first end 176 and a second end 182. Bight 180 will often include more than one loop, and may be pre-arranged so as to define a square knot (using the layout schematically illustrated in FIG. 18A), a clinch knot (FIG. 18B), or a variety of known or new surgical knots.

FIGS. 19A and 19B show the suture bight in the pre-deployed state (FIG. 19A) and the deployed state (FIG. 19B). Suture 502 is arranged with a bight 504 pre-arranged to form a pre-tied knot, a rail portion 540 and a non-rail portion 550. The suture 502 is arranged to provide bight 504 pre-arranged to form a pre-tied knot that automatically travels down from the shaft of the device 10 where it is stored prior to delivery to the tissue wall. The loop 503 of suture 502 serves to pull the knot 504 down the rail portion 540 of the suture during deployment. It should be noted that it would be desirable to be able to distinguish the ends 540 and 550 of the suture 502 during deployment so that the correct end is pulled by the operator to advance the knot. Should the non-rail end be pulled, the knot may be prematurely tightened before it is advance to its deployed position at the wall of the vessel.

The ends of the suture may be distinguished from each other by changing the color of one end (e.g. with dye), providing an attachment on one end (e.g. shrink wrap tubing, a bead, etc.) or with the suture itself (e.g. tying a knot in one end).

Figure 20:
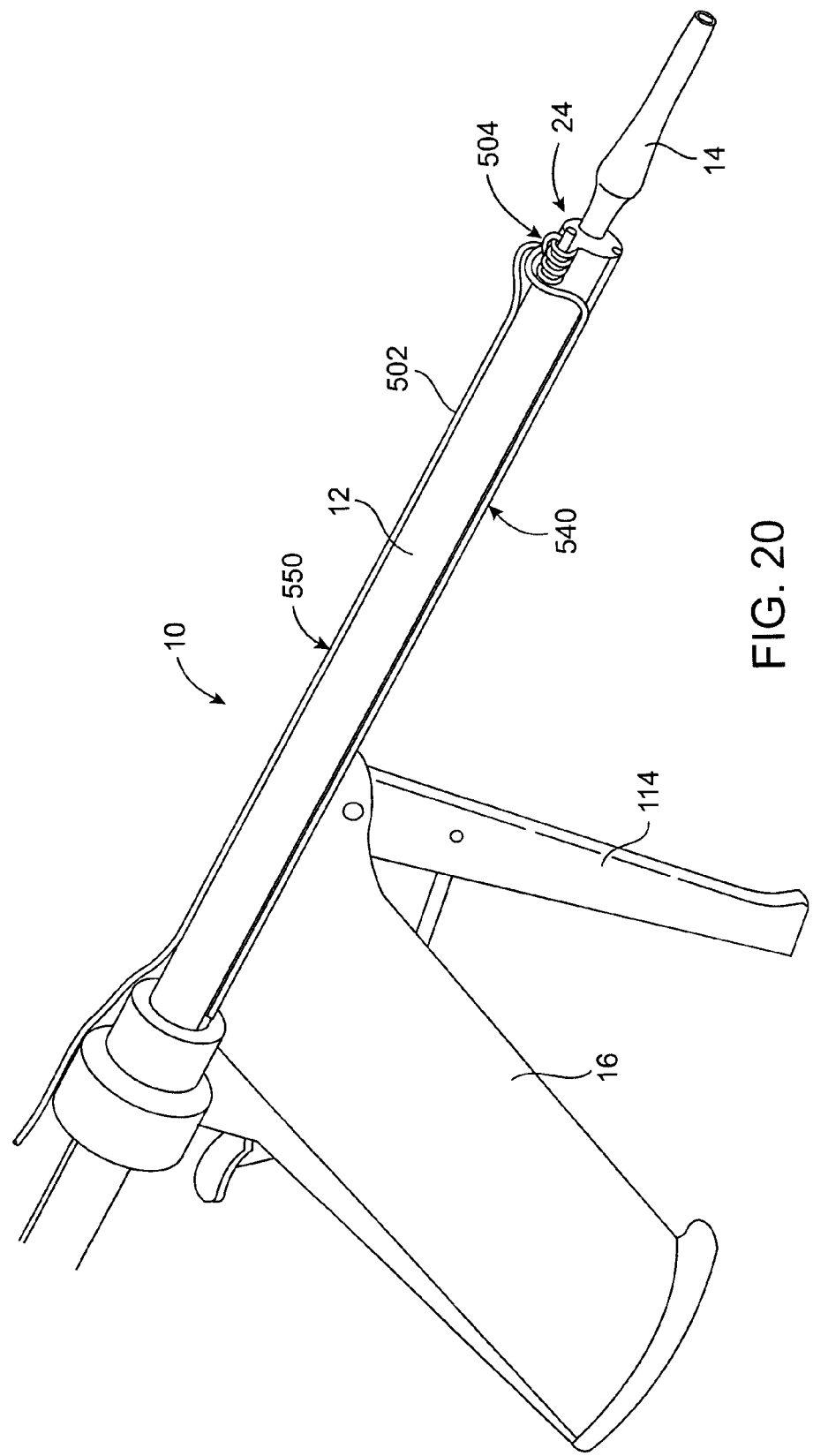
FIG. 20 is a perspective view of a suturing device incorporating a pre-tied knot.

FIG. 20 is a perspective view of an alternate embodiment of the invention, including a bight 504 pre-arranged to form a pre-tied knot. Suture applying device 10 includes shaft 12, nose piece 14, handle 16 and lever 114, as explained above. Suture 502 includes a bight 504 pre-arranged to form a pre-tied knot disposed around needle entry port 24, and a rail portion 540 and a non-rail portion 550. In various aspects, rail portion 540 may be disposed along a side release slot in shaft 12; however, the present invention is not so limited.

Figure 21:
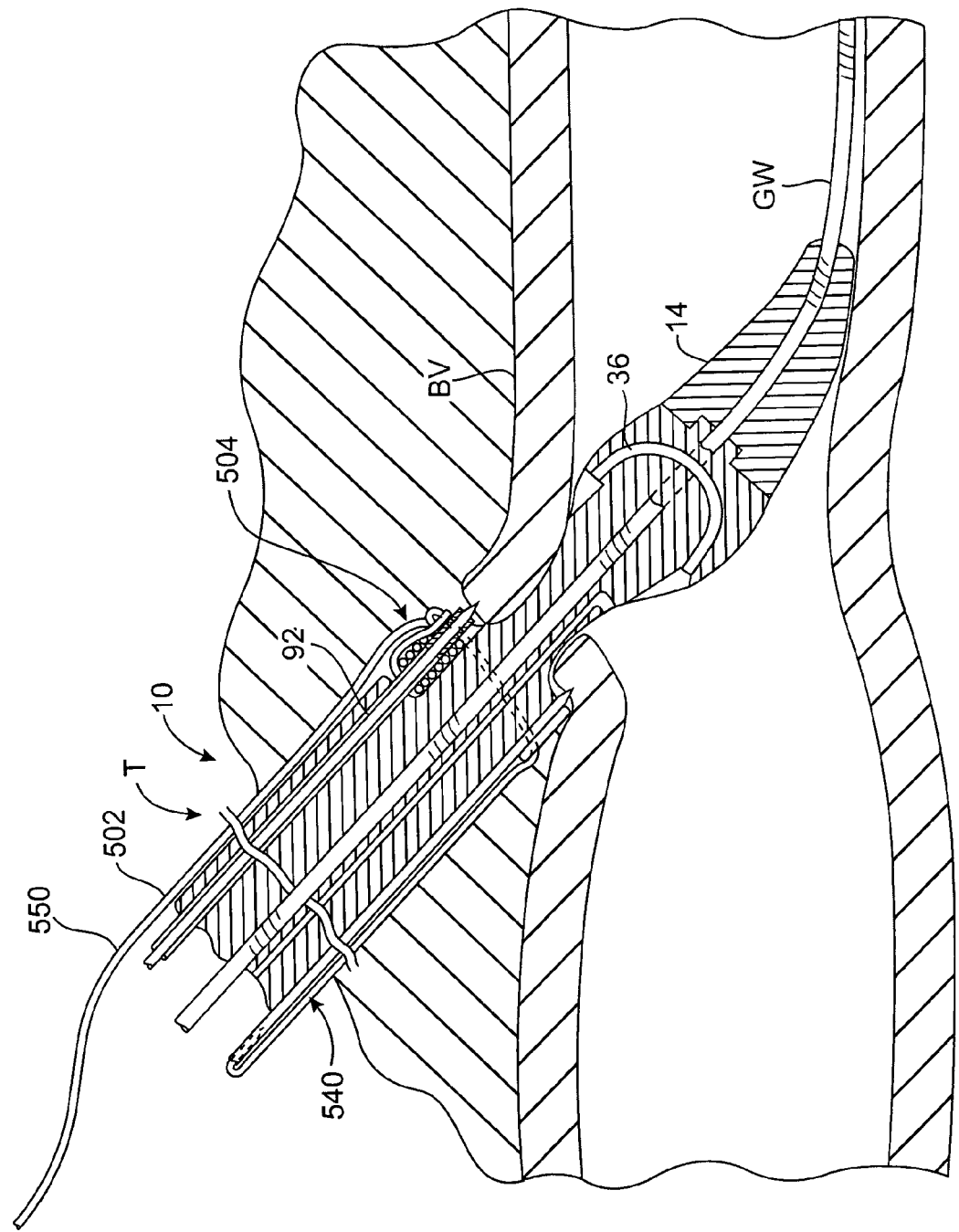
FIGS. 21 to 23 illustrate successive steps of advancing the suturing needle within the needle guide path of the needle guiding device of FIG. 20 in detail.

FIG. 21 shows the device of FIG. 20 in-situ prior to deployment. Referring now to FIGS. 21-24, use of the device 10 for applying end tying a suture loop in a blood vessel BV wall will be described in detail.

Referring in particular to FIG. 21, the device 10 is introduced through an existing tissue tract T, typically formed by an introducer sheath which has been previously placed in connection with a conventional percutaneous intravascular therapeutic or diagnostic procedure, such as angiography, angioplasty, atherectomy, laser ablation, cardiac mapping, cardiac ablation, or the like. As described above, suture 502 is disposed with rail portion 540 and non-rail portion 550 at opposite ends. Bight 504 is disposed between rail portion 540 and non-rail portion 550. The operation of nose piece 14, guide wire GW, stylet 92 and U-shaped return lumen 36 were described above in reference to other figures.

Figure 22:
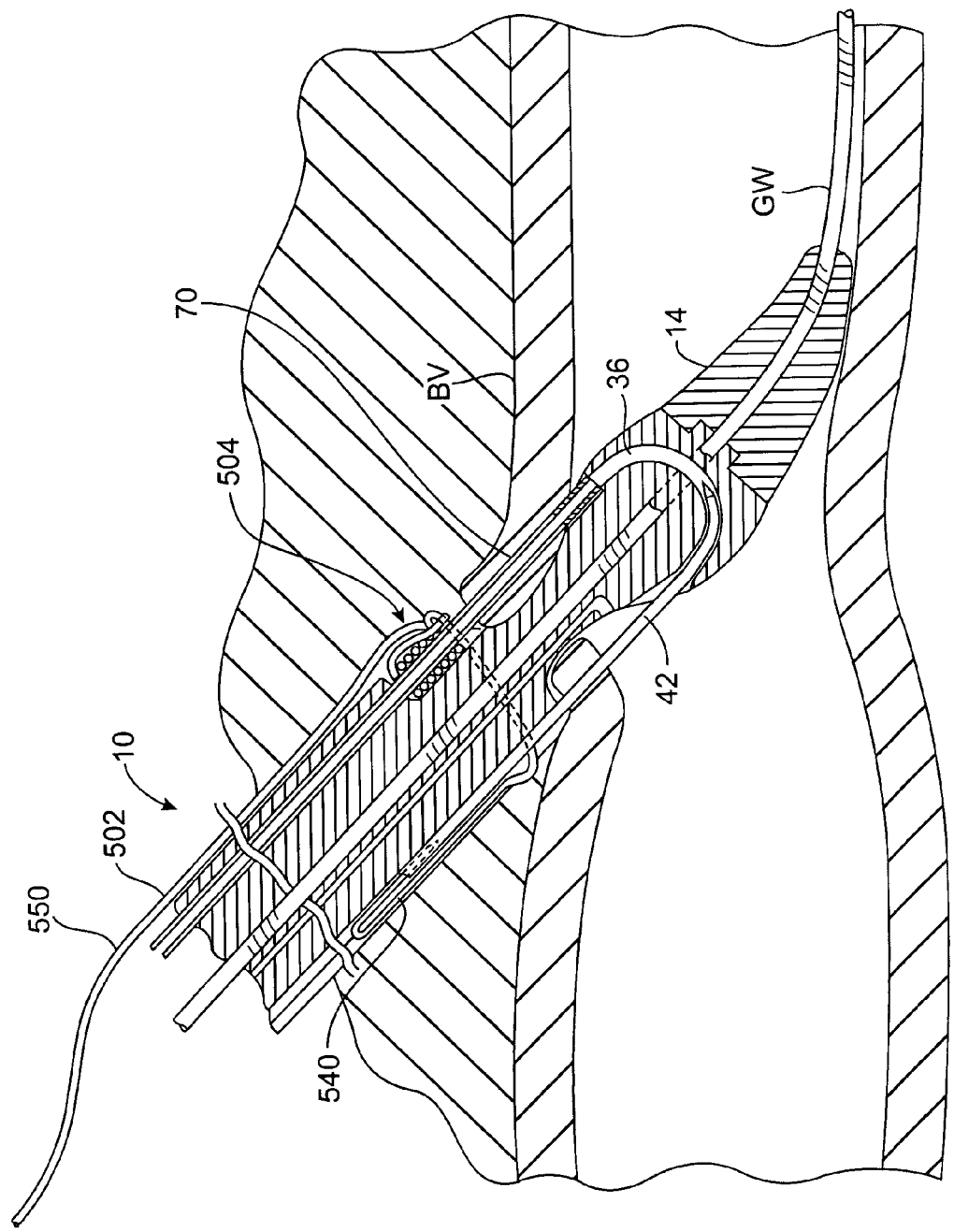
Figure 23:
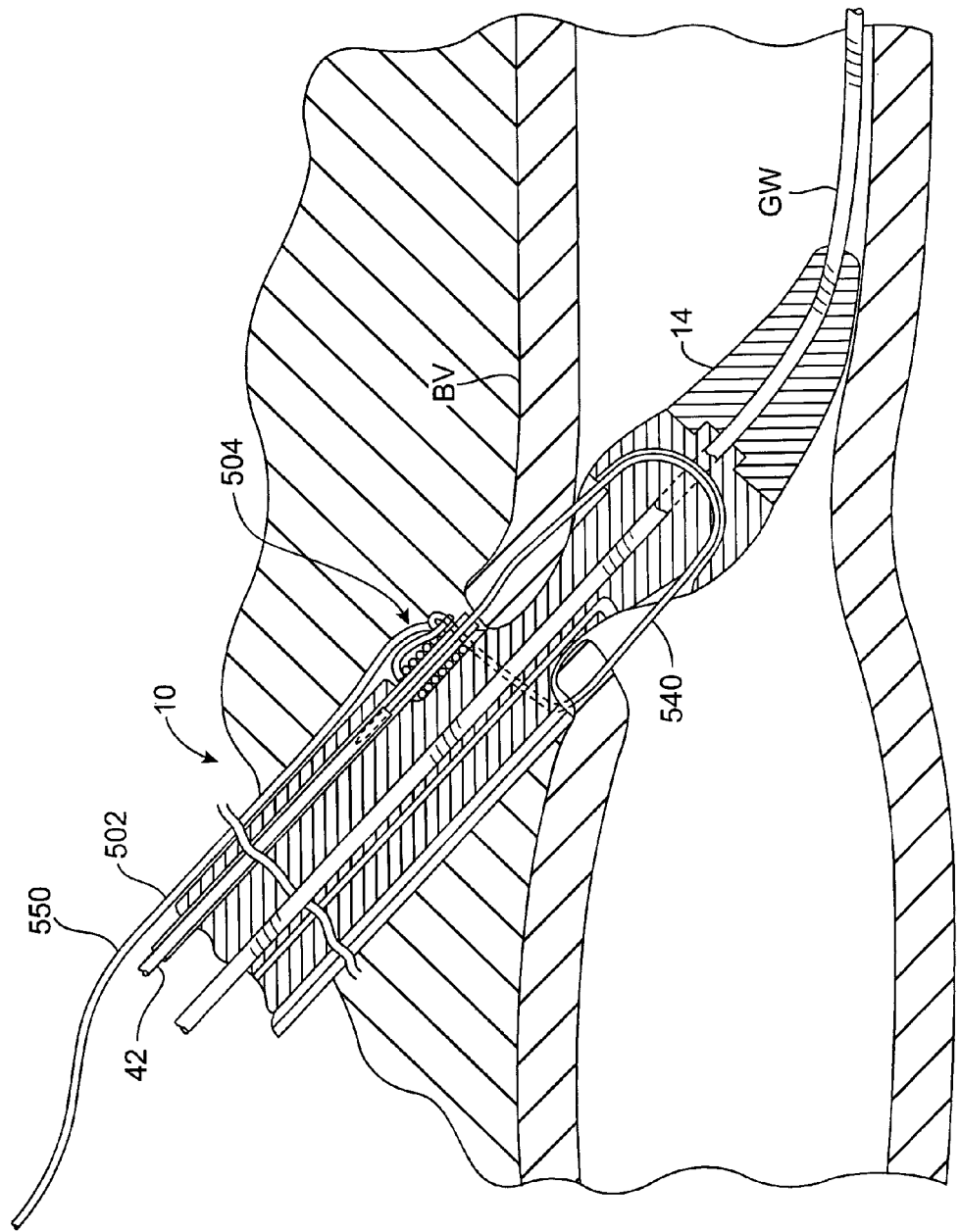
Figure 24:
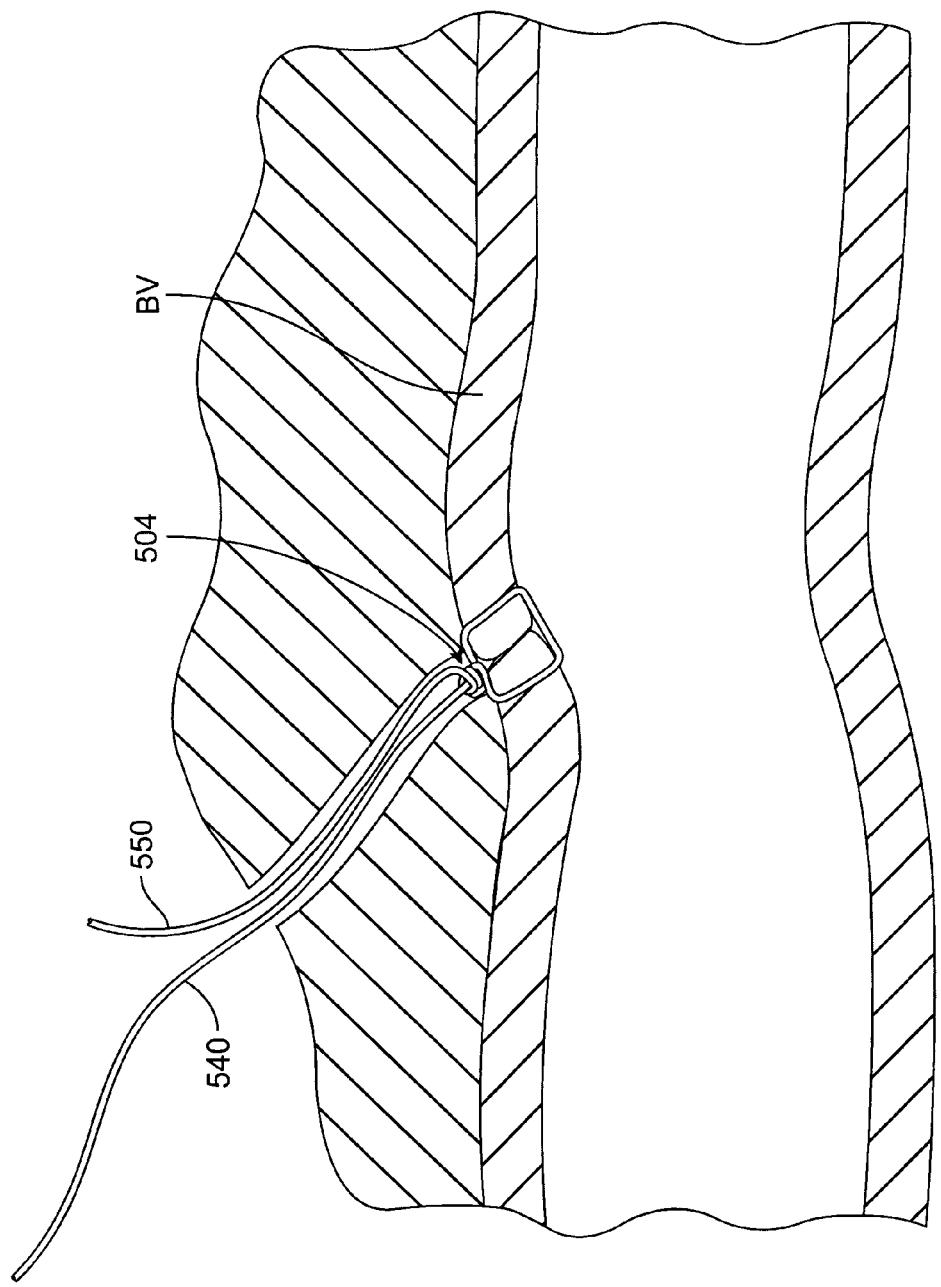
FIG. 24 illustrates a tied suture loop applied by the device of FIGS. 20 to 23 in the method of the present invention.

FIG. 22 illustrates subsequent advancement of needle guide tube 70 and advancement of flexible needle 42 through U-shaped lumen 36. FIG. 23 illustrates subsequent removal of flexible needle 42 pulling rail portion 540 of suture 502 through loops of bight 504 to form a pre-tied knot. Once suture 502 is released from the nose piece 14, the device 10 may be partially or totally withdrawn from the puncture into the blood vessel BV, leaving pre-tied knot 504, as illustrated in FIG. 24. Thus, ends 540 and 550 of suture 502 are accessible external to the tissue tract for securing suture 520 across the puncture to close the puncture.

Although the foregoing invention has been described in detail for purposes of clarity of understanding, it will be obvious that certain modifications may be practiced within the scope of the appended claims.

What is claimed is:

1. A method of closing a puncture in a blood vessel wall, the method comprising:
   positioning a suture placement device through the puncture in the blood vessel wall, the placement device having a length of suture with a first end, a second end and a bight between the first and second ends with the bight being prearranged on the device to define a pre-tied knot when the first end of the suture passes through the bight;
   advancing the first end of the length of suture in a distal direction from the device through a first penetration in the blood vessel wall adjacent to the puncture;
   guiding the suture length from the first penetration across a proximal side of the puncture to a second penetration adjacent to the puncture opposite the first penetration; and
   advancing the suture length in a proximal direction through the second penetration, through the device, and through the bight so that the two ends of the suture length are accessible for securing the suture across the puncture to close the puncture.

2. The method of claim 1, wherein advancing a length of suture in a distal direction comprises pushing a needle which carries the suture through the first penetration.

3. The method of claim 2, wherein guiding the suture length comprises elastically bending the needle as it tracks within the blood vessel to the second penetration.

4. The method of claim 3, wherein advancing the suture length in a proximal direction comprises pushing the needle so that a needle tip passes proximally out through the vessel wall adjacent the puncture.

5. A method for suturing a puncture site in a wall of a blood vessel, said method comprising:
   providing a suturing device having a pair of axially advanceable penetrating elements and a length of suture having a first end, a second end and a bight between the first and second ends, the bight being prearranged on the suturing device to define a pre-tied knot when the first end of the suture passes through the bight;
   advancing the penetrating elements to form two penetrations in the blood vessel wall on opposite sides of the puncture site;
   advancing the first end of the suture distally through the suture device, distally through one of the two penetrations into a lumen of the blood vessel, proximally through the other of the two penetrations, proximally through the suturing device, and through the bight; and
   securing the pre-tied knot to close the puncture site.

6. The method of claim 5, wherein the penetrating elements are needle guides.

7. The method of claim 6, wherein advancing the suture comprises pushing the suture distally through a lumen of a first needle guide tube and pulling the suture proximally through a second needle guide tube.

8. The method of claim 7, wherein advancing the suture comprises providing a needle having the suture attached thereto and pushing the needle distally through the lumen of the first needle guide tube and pulling the needle proximally through the second needle guide tube.

9. A method of suturing a puncture site in a wall of a blood vessel, said method comprising:
  providing a length of suture having a first end, a second end and a bight between the first and second ends, the bight being prearranged and adapted to receive the first end therethrough to define a pre-tied knot when the first end of the suture passes through the bight;
  pushing the suture distally through a tissue tract over the puncture site through a penetration on one side of the puncture site into a lumen of the blood vessel;
  pulling the suture proximally through a second penetration on another side of the puncture site and proximally through the tissue tract;
  passing the suture through the bight; and
  securing the pre-tied knot to close the puncture site.

10. The method of claim 9, wherein the bight is prearranged around a needle in the device.

11. The method of claim 9, wherein the length of suture is advanced in a distal direction by pushing a needle which carries the length of suture through the first penetration.

12. The method of claim 11, wherein the length of suture is guided by elastically bending the needle as it tracks within the blood vessel to the second penetration.

* * * * *

UNITED STATES PATENT AND TRADEMARK OFFICE
CERTIFICATE OF CORRECTION

| | | |
|---|---|---|
| PATENT NO. | : 7,390,328 B2 | Page 1 of 1 |
| APPLICATION NO. | : 10/742406 | |
| DATED | : June 24, 2008 | |
| INVENTOR(S) | : Modsesitt | |

It is certified that error appears in the above-identified patent and that said Letters Patent is hereby corrected as shown below:

Col. 12
Line 47 change "Peach" to --each--

Col. 13
Line 12 change "bight 502" to --bight 504--

Col. 15
Line 16 change "Fig. 18A" to --Fig. 18B--
Line 16 change "Fig. 18B" to --Fig. 18A--
Line 32 change "advance" to --advanced--

Signed and Sealed this

Twenty-sixth Day of January, 2010

David J. Kappos
*Director of the United States Patent and Trademark Office*